US008753625B2

(12) United States Patent
Fung et al.

(10) Patent No.: US 8,753,625 B2
(45) Date of Patent: *Jun. 17, 2014

(54) USE OF COMPLEMENT INHIBITORS TO TREAT OCULAR DISEASES

(75) Inventors: Sek Chung Fung, Gaithersburg, MD (US); Zhengbin Yao, Berwyn, PA (US)

(73) Assignee: Genentech, Inc., South San Francisco, CA (US)

( * ) Notice: Subject to any disclaimer, the term of this patent is extended or adjusted under 35 U.S.C. 154(b) by 1047 days.

This patent is subject to a terminal disclaimer.

(21) Appl. No.: 12/092,346

(22) PCT Filed: Nov. 4, 2006

(86) PCT No.: PCT/US2006/043103
§ 371 (c)(1),
(2), (4) Date: Oct. 9, 2008

(87) PCT Pub. No.: WO2007/056227
PCT Pub. Date: May 18, 2007

(65) Prior Publication Data
US 2009/0214538 A1 Aug. 27, 2009

Related U.S. Application Data

(60) Provisional application No. 60/733,763, filed on Nov. 4, 2005.

(51) Int. Cl.
*A61K 39/395* (2006.01)
*A61K 39/00* (2006.01)

(52) U.S. Cl.
USPC ..................... 424/130.1; 424/133.1

(58) Field of Classification Search
None
See application file for complete search history.

(56) References Cited

U.S. PATENT DOCUMENTS

| | | | |
|---|---|---|---|
| 4,816,567 A | 3/1989 | Cabilly | |
| 5,456,909 A | 10/1995 | Marsh et al. | |
| 5,534,615 A | 7/1996 | Baker et al. | |
| 5,624,837 A | 4/1997 | Fordor et al. | |
| 5,627,264 A | 5/1997 | Fodor et al. | |
| 5,679,546 A | 10/1997 | Ko et al. | |
| 5,679,564 A | 10/1997 | Pace et al. | |
| 5,851,528 A | 12/1998 | Ko et al. | |
| 5,853,722 A | 12/1998 | Rollins et al. | |
| 5,856,297 A | 1/1999 | Fearon et al. | |
| 5,856,300 A | 1/1999 | Rittershaus et al. | |
| 5,858,969 A | 1/1999 | Marsh et al. | |
| 5,861,156 A | 1/1999 | George et al. | |
| 6,333,034 B1 | 12/2001 | Gupta-Bansal et al. | |
| 6,407,213 B1 | 6/2002 | Carter et al. | |
| 6,410,708 B1 | 6/2002 | Ashkenazi et al. | |
| 6,472,520 B2 | 10/2002 | Fisher | |
| 6,534,058 B2 | 3/2003 | Fung | |
| 6,569,992 B1 | 5/2003 | LaFleur et al. | |
| 6,642,353 B1 | 11/2003 | McConnell et al. | |
| 6,838,554 B2 | 1/2005 | Ashkenazi et al. | |
| 6,956,107 B2 | 10/2005 | Fung et al. | |
| 7,112,327 B2 * | 9/2006 | Fung et al. | 424/154.1 |
| 7,192,589 B2 | 3/2007 | Ashkenazi et al. | |
| 7,211,400 B2 | 5/2007 | Ashkenazi et al. | |
| 7,282,565 B2 | 10/2007 | Goddard et al. | |
| 7,419,663 B2 | 9/2008 | Ashkenazi et al. | |
| 7,432,356 B2 | 10/2008 | Fung et al. | |
| 7,439,331 B2 | 10/2008 | Fung et al. | |
| 7,943,135 B2 | 5/2011 | Fung et al. | |
| 8,007,791 B2 | 8/2011 | Hass et al. | |
| 8,124,090 B2 | 2/2012 | Fung et al. | |
| 8,193,329 B2 | 6/2012 | An et al. | |
| 8,236,317 B2 | 8/2012 | Fung et al. | |
| 8,268,310 B2 | 9/2012 | Hass et al. | |
| 8,273,352 B2 | 9/2012 | Huang et al. | |
| 8,372,403 B2 | 2/2013 | An et al. | |
| 8,383,802 B2 | 2/2013 | Fung et al. | |
| 2003/0129187 A1 | 7/2003 | Fung et al. | |
| 2003/0207309 A1 * | 11/2003 | Hageman et al. | 435/6 |
| 2004/0152105 A1 | 8/2004 | Vogt et al. | |
| 2005/0191298 A1 | 9/2005 | Bell et al. | |
| 2005/0197285 A1 | 9/2005 | Rosen et al. | |
| 2005/0222027 A1 | 10/2005 | Chiang et al. | |

(Continued)

FOREIGN PATENT DOCUMENTS

| | | |
|---|---|---|
| EP | 0 239 400 | 3/1994 |
| RU | 2232991 | 7/2004 |

(Continued)

OTHER PUBLICATIONS

Zeng et al., "Lack of association of CFD polymorphisms with advanced age-related macular degeneration" Molecular Vision 16:2273-2278 (2010).*
U.S. Appl. No. 09/253,689, filed Feb. 20, 1999, Fung et al.
Accession NM_001928 "*Homo sapiens* complement factor D (adipsin) (cFD), mRNA" dated Mar. 12, 2011.
Aderem et al., 1999, "Mechanisms of phagocytosis in macrophages." Annu. Rev. Immunol. 17: 593-623.
Akif et al., 2002, "Novel anti-factor D monoclonal antibody inhibits complement and leukocyte activation in baboon model of cardiopulmonary bypass." Annals of Thoracic Surgery 74(2):355-362.
Amersterdam et al., 1995, "Limitation of reperfusion injury by a monoclonal antibody to C5a during myocardial infarction in pigs." Am. J. Physiol. 268(1 Pt 2): H448-57.

(Continued)

*Primary Examiner* — Daniel E Kolker
*Assistant Examiner* — James Rogers
(74) *Attorney, Agent, or Firm* — Jones Day

(57) ABSTRACT

The present invention relates to the treatment of ocular diseases and conditions by administering a complement pathway inhibitor, particularly an alternative pathway inhibitor. Ocular diseases include age-related macular degeneration, diabetic retinopathy, and ocular angiogenesis. One embodiment comprises the administration of an anti-Factor D antibody in the form of a whole antibody, a Fab fragment or a single domain antibody. Other complement component inhibitors that may be useful in the present method include Factor H or inhibitors that block the action of properdin, factor B, factor Ba, factor Bb, C2, C2a, C3a, C5, C5a, C5b, C6, C7, C8, C9, or C5b-9.

38 Claims, No Drawings

(56) References Cited

U.S. PATENT DOCUMENTS

| | | | |
|---|---|---|---|
| 2006/0067935 A1* | 3/2006 | Ambati | 424/144.1 |
| 2006/0233803 A1 | 10/2006 | Ashkenazi et al. | |
| 2006/0240020 A1 | 10/2006 | Fung et al. | |
| 2007/0077233 A1* | 4/2007 | Giordano | 424/93.2 |
| 2007/0098692 A1* | 5/2007 | Kovesdi et al. | 424/93.2 |
| 2007/0190054 A1* | 8/2007 | Ashkenazi et al. | 424/145.1 |
| 2008/0118506 A1* | 5/2008 | An et al. | 424/133.1 |
| 2009/0269338 A1 | 10/2009 | Huang et al. | |
| 2011/0123528 A1* | 5/2011 | An et al. | 424/133.1 |
| 2011/0165622 A1 | 7/2011 | An et al. | |
| 2011/0195069 A1 | 8/2011 | Fung et al. | |
| 2012/0328613 A1 | 12/2012 | Huang et al. | |
| 2013/0171070 A1 | 7/2013 | An et al. | |

FOREIGN PATENT DOCUMENTS

| | | |
|---|---|---|
| WO | WO 95/29697 | 11/1995 |
| WO | WO 99/27098 | 3/1999 |
| WO | WO 99/40100 | 8/1999 |
| WO | WO 99/42133 | 8/1999 |
| WO | WO 99/46281 | 9/1999 |
| WO | WO 00/12703 | 3/2000 |
| WO | WO 00/37638 | 6/2000 |
| WO | WO 00/42072 | 7/2000 |
| WO | WO 00/53749 | 9/2000 |
| WO | WO 00/53758 | 9/2000 |
| WO | WO 01/04311 | 1/2001 |
| WO | WO 01/36432 | 5/2001 |
| WO | WO 00/36102 | 6/2001 |
| WO | WO 01/40466 | 6/2001 |
| WO | WO 02/00690 | 1/2002 |
| WO | WO 02/08284 | 1/2002 |
| WO | WO 02/30985 | 4/2002 |
| WO | WO 02/30986 A2 | 4/2002 |
| WO | WO 2004/014953 | 2/2004 |
| WO | WO 2004/022594 | 3/2004 |
| WO | WO 2005/025509 | 3/2005 |
| WO | WO 2005/102387 | 11/2005 |
| WO | WO 2006/042329 | 4/2006 |
| WO | WO 2006/062716 | 6/2006 |
| WO | WO 2006/071856 | 7/2006 |
| WO | WO 2006/088950 | 8/2006 |
| WO | WO 2007044668 A2 * | 4/2007 |
| WO | WO 2007/053447 | 5/2007 |
| WO | WO 2007/056227 | 5/2007 |
| WO | WO 2007/087384 | 8/2007 |
| WO | WO 2008/055206 | 5/2008 |
| WO | WO 2008/147883 | 12/2008 |
| WO | WO 2009/134711 | 11/2009 |

OTHER PUBLICATIONS

Amit et al., 1986 "Three dimensional Structure of an Antigen-Antibody Complex at 2.8A Resolution." Science 233:747-753.
Arrate et al., 2001, "Cloning of human junctional adhesion molecule 3 (JAM3) and its identification as the JAM2 counter-receptor." J Biol. Chem.. 276(49):45826-45832.
Attwood, 2000, "The Babel of bioinformatics." Science 290:471-473.
Barnum et al., 1984, "Quantification of complement factor D in human serum by a solid phase radioimmunoassay." Immunol Methods 67(2):303-9.
Bertozzi et al., 1997, "An ELISA for selectins based on binding to a physiological ligand." J. Immunol. Methods 203(2):157-65.
Blast Report, http://expasy.org/egi-bininiceprot.pl/printable?ac=Q80WA3, dated Mar. 1, 2004.
Brown et al., 2007, "Mechanisms of disease: the complement system in renal injury—new ways of looking at an old foe." Nat Clin Pract Nephrol. 3(5):277-86.
Brown, 1992, "Complement receptors, adhesion, and phagocytosis," Infectious agents and disease, 1:63-70.
Carroll, 2004, "The complement system in regulation of adaptive immunity." Nat. Immunol. 5(10):981-986.
Carter et al., "Humanization of an anti-p185HER2 antibody for human cancer therapy". Proc. Natl. Acad. Sci. USA, 89:4285-4289 (1992).
Casset et al., 2003, "A peptide mimetic of an anti-CD4 monoclonal antibody by rational design." Biochem Biophys Res Comm. 307:198-205.
Chample et al., 1995, "Monoclonal antibodies that block the activity of leukocyte function-associated antigen 1 recognize three discrete epitopes in the inserted domain of CD11a" J Biol. Chem. 270:1388-1394.
Chen et al, 1999, "Selection and analysis of an optimized anti-VEGF antibody: crystal structure of an affinity-matured Fab in complex with antigen." J Mol. Biol. 293:865-881.
Chothia et al., "Canonical structures for the hypervariable regions of immunoglobulins." J. Mol. Biol., 196:901-917 (1987).
Database Genbank (Apr. 24, 2001), "Human Pro 1868 Protein" Database Accession No: AAB80272 XP002448361, dated Jun. 15, 2007.
Edwards et al., 2005, "Complement factor H polymorphism and age-related macular degeneration," Science 308: 419-421.
Evans et al., "Rapid Expression of an Anti-Human C5 Chimeric Fab Utilizing a Vector that Replicates in COS and 293 Cells," J. Immunol., 184: 123-138 (1995).
Ferris et al., 2005, "A simplified seveity scale for age-related macular degeneration," Arch Opthalmol. 123:1570-74.
Fung, M. et al., 2000, "Inhibition of Complement, Neutrophil, and Platelet Activation by an Anti-Factor D Antibody During Extracorporeal Circulation". Presented in the 18th Annual Houston Conference on Biomedical Engineering Research, Houston, Texas. Feb. 10-11, 2000 (Abstract).
Gao et al., 1995, "An enzyme-linked immunosorbent assay to identify inhibitors of activation of platelet integrin alpha IIb beta 3" J. Immunol. Methods. 181(1):55-64.
Hageman et al., 2005, "A common haplotype in the complement regulatory gene factor H (HF1/CFH) predisposes individuals to age-related macular degeneration." Proc. Natl. Acad Sci. 102(20): 7227-7232.
Hakimi et al., 1991, "Reduced immunogenicity and improved pharmacokinetics of humanized anti-Tac in cynomolgus monkeys". J. Immunol., 147(4):1352-1959.
Harboe et al., "The quantitative role of alternative pathway amplification in classical pathway induced terminal complement activation." Clinical and Experimental Immunology, 138(3):439-446 (2004).
Harlow et al., 1988, "Chapter 14: Immunoassays." Antibodies, A Laboratory Manula. Cold spring harbor pp. 553-612.
Haubenwallner et al., "A novel missense mutation in the gene for lipoprotein lipase resulting in a highly conservative amino acid substitution ($Asp^{180}$ →Glu) causes familial chylomicronemia (type I hyperlipoproteinemia)" Genomics, 18(2):392-396 (1993).
Holers et al., 1992, "The evolution of mouse and human complement C3-binding proteins: divergence of form but conversation of function." Immnol. Today 13(6):231-236.
Holm et al., 2007, "Functional mapping and single chain construction of the anti-cytokeratin 8 monoclonal antibody TS1." 44(6):1075-1084.
Homeister et al., 1993, "Soluble complement receptor type 1 prevents human complement-mediated damage of the rabbit isolated heart" J. Immunol. 150(3):1055-64.
Houghten et al., 1992, "the use of synthetic peptide combinatorial libraries for the identification of bioactive peptides." Biotechniques 13(3):412-21.
Huber-Lang et al., "Role of C5a in Multiorgan Failure During Sepsis" J. of Immunology, 166:1193-1198 (2001).
Ingai et al., 1993, "Decreased Activity of Complement-Mediated Immune Complex Clearance in Hemodialysis Patients," Clin. Immune & Immunopath. 68(3):333-339.
Jaffe et al., 2006 Intraocular Drug Delivery. Taylor and Francis pp. 85-95,111-128, 193-202,203-255,249-263.
Jaffers et al., "Monoclonal antibody therapy. Anti-idiotypic and non-anti-idiotypic antibodies to OKT3 arising despite intense immunosuppression". Transplantation 41(5):572-578 (1986).
Jager et al., 2008, "Age-related macular degeneration." New Engl J med. 359(16): 1735-6.

(56) References Cited

OTHER PUBLICATIONS

Janeway et al., 1997,*Immunobiology* (13-5 to 13-7) 3*rd* edition, London, Eng Current Biology ltd.
Janssen et al., 2007, "Structural insights into the central complement component C3." Molec. Immunol. 44:3-10.
Jones et al., "Replacing the complementarity-determining regions in a human antibody with those from a mouse." Nature, 321:522-525 (1986).
Junghans et al., "Anti-Tac-H, a humanized antibody to the interleukin 2 receptor with new features for immunotherapy in malignant and immune disorders". Cancer Res. 50:1495-1502 (1990).
Katschke et al., 2007, "A Novel inhibitor of the alternative pathway of complement reverses inflammation and bone destruction in experimental arthritis." Brief Definitive Report 204(6): 1319-1325.
Khazaeli et al., "Phase 1 trial of multiple large doses of murine monoclonal antibody CO17-1A. II. Pharmacokinetics and immune response". J. Natl. Cancer Inst. 80:937-942 (1988).
Kim et al., 2005, "Characterization of monoclonal antibody specific to the Z3291g protein, a member of immunoglobulin superfamily." Immunol. Letters 99:153-161.
Klein et al., 2005, "Complement Factor H Variant Increases the Risk of Age-Related Macular Degeneration," Science, 308:385-389.
Klohs et al., 1997, "Inhibitors of tyrosine kinase." Curr. Opin. Oncol. 19 9(6):562-8.
Kostavasilli et al., 1997, "Mechanism of complement inactivation by glycoprotein c of herpes simplex virus." Immunol. 158(4): 1763-71.
Kroshus et al., 1995, "Complement inhibition owith an anti-C5 monoclonal antibody prevents acute cardiac tissue injry in an ex vivo model of pig-to-human xenotransplatation." Transplantation 60(11):1194-202.
Lam et al., 1997, "Application of combinatorial library methods in cancer research and drug discovery." Anticancer Drug Des 12(3): 145-67.
Langnaese et al., 2000, "Cloning of Z39Ig, a novel gene with immunoglobulin-like domains located on human chromosome XI" BBA, 552-555.
Laubser et al., "Inhibition of Complement, Neutrophil, and Platelet Activation by an Anti-Factor D Antibody During Extracorporeal Circulation", Presented at the Annual Meeting of American Society of Anestesiologists, San Francisco, California, Oct. 14-18, 2000 (Abstract A-657).
Lee et al., 2006, "Z39 1g is expressed on macrophages and may mediate inflammatory reactions in arthritis and artherosclerosis." J of Leukocyte boil. 80: 922-928.
MacCallum et al., 1996, "Antibody-antigen interactions: contact analysis and binding site topography" J Mol Bol 262:732-745.
Makrides et al., 1998, "Therapeutic Inhibition of the Complement System." Pharmacological Reviews. 50(1):59-87.
Matson et al., 2000, "Evolving concepts of therapy for sepsis and septic shock and the use of hyperpermeable memberanes", Current Opinion in Critical Care 6:431-436.
Miller et al., "Monoclonal antibody therapeutic trials in seven patients with T-cell lymphoma". Blood, 62:988-995 (1983).
Morgan, 1994, "Clinical complementology: recent progress and future trends." Eur J. Clin Invest 24(4):219-28.
Morley & Walport, 2000, "Factor D" Complements Facts Book, 17, 69-72.
Mulligan et al., "Protective Effects of Soluble CR1 in Complement and Neutrophil-Medicated Tissue Injury", J. Immunol., 148(5):1479-1485 (1992).
Narayana et al., "Structure of Human Factor D:A Complement System Protein at 20.degree. Resolution", J. Mol. Biol., 235: 695-708 (1994).
Niemann et al., "The Use of Monoclonal Antibodies as Probes of the Three Dimensional Structure of Human Complement Factor D", J. Immunol., 132(2): 809-815 (1984).
Omer et al., 1997, "CA1A2X-competitive inhibitors of farnesyltransferase as anti-cancer agents" Trends Pharmacol Sci. 18(11):434-44.
Padlan et al, 1989, "Structure of an antibody-antigen complex: crystal structure of the HyHEL-10 Fab-lysozyme complex." Proc. Natl. Acad Sci 1989:5938-5942.
Pascual et al., 1988, Metabolism of complement factor D in renal failure. Kidney International 34(4):529-36.
Pascual et al., 1990, "A monoclonal which antibody which blocks the function of factor D of human complement." J Immunol. Methods 127(2)263-9.
Pascual et al., 1993, "Inhibition of complement alternative pathway in mice with Fab antibody to recombinant adipsin/factor D." Eur J. Immunol. 23(6): 1389-92.
Paul, 1993, Fundamental Immunology, 3*rd* edition, raven press. 292-295.
Petrukhin et al., 2007, "New therapeutic targets in atrophic age-relaed macular degeneration." Expert Opinion on Therapeutic targets 11(5):625-639.
Powell et al., 1996, "A compendium and hydropathy/flexibility analysis of common reactive sites in proteins: reactivity at Asn, Asp, Gin, and Met motifs in neutral pH solution" Pharm Biotech 9:1-140.
Pyz et al., 2006, "C-type lectin-like receptors on myeloid cells." Annals of Med 38:242-251.
Rabinovici et al., 1992, "role of compleent in endotoxin/platelet-activating factor-induced lung injyr." J. Immunol. 149(5):1744-50.
Ray et al., 1997, "Thrombin receptor: a novel target for antiplatelet drug development" Thromb Res. 87(1): 37-50.
Ricklin and Lambris, 2007, "Complement-targeted therapeutics." Nat Biotechnol. 25(11):1265-75.
Riechmann et al., "Reshaping human antibodies for therapy". Nature, 332:323-327 (1988).
Rinder et al., 1995, "Blockade of C5a and C5b-9 generation inhibits leukocyte and platelet activation during extracorporeal circulation." J. clin. Invest. 96(3):1564-72.
Roiirer et al., 2009, "A targeted inhibitor of the alternative complement pathway reduces angiogenesis in a mouse model of age-related macular degeneration." Invest Ophthalmol Vis Sci. (7):3056-64.
Ross et al., 1985, "Membrane complement receptors specific for bound fragments of C3." Advances in Immunol. 37:217-267.
Rudikoff et al., 1982, "Single amino acid substitution altering antigen-binding specificity." Proc. Natl. Acad Sci 79(6):1979-1983.
Sahu et al., 1993, "Identification of multiple sites of interaction between heparin and the complement system" Mol. Immunol. 30(7): 679-84.
Sallo et al., 2009, "The International Classification system and the progression of age-related macular degeneration." Curr Eye. Res. 34(3):238-40.
Sato et al., 1997, "A new method for studying the binding of human IgE to CD23 and the inhibition of this binding." J Immunol. Methods 209(1): 59-66.
Sears et al., "Effects of monoclonal antibody immunotherapy on patients with gastrointestinal adenocarcinoma". J. Biol. Response Modifiers. 3:138-150 (1984).
Shawler et al., Human immune response to multiple injections of murine monoclonal IgG. J. Immunol. 135(2):1530-1535 (1985).
Sim et al., "Serine Proteases of the Complement System", Biochemical Society Transactions, vol. 28, Pt.5, pp. 545-550 (2000).
Sims et al., "A humanized CD18 antibody can block function without cell destruction". J. Immunol., 151(4):2296-2308 (1993).
Skolnick et al., 2000, "From genes to protein structure and function: novel applications of computational approaches in the genomic era." Trends in Biotech 18: 34-39.
Stadel et al., 1997, "Orphan G protein-coupled receptors: a neglected opportunity for pioneer drug discovery"Trends Pharmacol. Sci 18(11): 430-7.
Strausberg et al., 2002, "Generation and initial analysis of more than 15,000 full-length human and mouse cDNA se uences," Proc. Natl. Acad Sci. 99:26-16899-16903.
Strawn et al., 1996, "Fik-1 as a target for tumor growth inhibition." Cancer Res. 56(15):3540-5.
Stuart et al., 2005, "Phagocytosis: Elegant complexity." Immunity 22:539-550.
Tanhehco et al., 1999, "The anti-factor D antibody, MAb 166-32, inhibits the alternative pathway of the human complement system." Transplant Proc. 31(5):2168-71.

(56) References Cited

OTHER PUBLICATIONS

Taylor et al., 2003, "Pattern recognition receptors and differentiation antigens define murine myeloid cell heterogeneity cx vivo." Eur. J. Immunol. 33:2090-2097.
Taylor et al., 2005, "Macrophage receptors and immune recognition", Annu. Rev. ImmunoL, 23: 901-944.
Thurman et al., 2006, "The central role of the alternative complement pathway in human disease." J immunol. 176:1305-1310.
Tsukita et al., 2001, "Multifunctional strands in tight junctions." Nat. Revew. 2:285-293.
Ündar et al., "Novel Anti-Factor D Monoclonal Antibody Inhibits Complement, Neutrophil, and Platelet Activation in a Simulated Pediatric Cardiopulmonary Bypass Circuit"., Presented in the 46$^{th}$ Annual Conference of the American Society for Artificial Internal Organs, New York, N. Y., Jun. 28-Jul. 1, 2000, (Abstract).
Underhill eta l., 2002, "Phagocytosis of microbes: Complexity in action." Annu Rev. Immunol. 20:825-852.
Vajdos et al., 2002, "Comprehensive functional maps of the antigen-binding site of an anti-ErbB2 antibody obtained with shotgun scanning mutagenesis." J. Mol. Biol. 320(2):415-428.
Verhoeyen et al., "Reshaping human antibodies: grafting an antilysozyme activity". Science, 239:1534-1536 (1988).
Volanakis et al., "Complement Enzymes", In: *The Human Complement System in Health & Disease,* Chapter 4, pp. 49-81, Eds., J. Volonakis & M. M. Frank, Published by Marcel Dekker, Inc. New York (1998).
Volanakis et al., "Complement Factor D, A Novel Serine Protease", Protein Science, 5:553-564 (1996).
Walker et al., 2002, "Z391g is co-expressed with activation macrophage genes." Biochemica et Biophysica Acta 1574:387-390.
Walport, 2001 "Complement first of two parts." Advances in lmmunol. Neng J med 344(14): 1058-1066.
Wang et al., 1995, "Anti-C5 monoclonal antibody therapy prevents collage-induced arthritis and ameliorate established disease." Proc. Nalt. Acad Sci. 92(19):8955-9.
Weisman et al., 1990, "Soluble human complement receptor type 1: in vivo inhibitor of complement suppressing post-ischemic myocardial inflammation and necrosis." Science 249(4965):146-51.
Weisman et al., 2006, "Structure of C3b in complex with CRIg gives insignt into regulation of complement activation." Nature 444(7116):217-20.
White et al., "Human Adipsin is Identical to Complement Factor D and is Expressed at Iligh Levels in Adipose Tissue", J. Bio. Chem, 267(13): 9210-9213 (1992).
Wilson et al., 1993, "A competitive inhibition ELISA for the quantification of human interferon-gamma" J. Immuonl. Methods 162(2):247-55.
Wu et al., 1999, "Humanization of a murine monoclonal antibody by simultaneous optimization of framework and CRD residues." JMB 294:151-162.
Bora et al., 2006, "Complement activation via alternative pathway is critical in the development of laser-induced choroidal neovascularization: role of factor B and factor H." J. Immunol. 177:1872-8.
International Search Report dated Aug. 10, 2007 of PCT/US06/043103, now WO 2007/056227.
Written Opinion dated Aug. 10, 2007 of PCT/US06/043103, now WO 2007/056227.
International Preliminary Examination Report, dated Nov. 24, 2009 of PCT/US2008/064526, now WO 2008/147883.
International Search Report, dated Aug. 14, 2008, of PCT/US2008/064526, now WO 2008/147883.
Written Opinion dated Nov. 24, 2009 of PCT/US2008/064526, now WO 2008/147883.
International Preliminary Report on Patentability, dated May 2, 2009, of PCT/US2007/083172 now, WO 2008/055206.
International Search Report, dated Jun. 26, 2008, of PCT/US2007/083172 now, WO 2008/055206.
Written Opinion dated May 2, 2009, of PCT/US2007/083172 now, WO 2008/055206.
International Search Report dated Sep. 15, 2009 of PCT/US09/41785, now WO 2009/134711.
Written Opinion dated Oct. 28, 2010 of PCT/US09/41785, now WO 2009/134711.
Notice of Allowance, dated Jun. 23, 2011 in U.S. Appl. No. 11/931,060 now published as U.S. 2008/0188506.
Notice of Allowance, dated Sep. 28, 2011 in U.S. Appl. No. 13/,007,061 now published as U.S. 2011/0165622.
Notice of Allowance, dated Sep. 29, 2011 in U.S. Appl. No. 13/,007,142 now published as U.S. 2011/0123528.
Ambati, J. et al., An animal model of age-related macular degeneration in senescent Cel-2- or Cer-2-deficient mice. Nat. Med., Nov. 2003; 9(11):1390-7 Epub 2003 Oct. 19).
Anderson, D.H., et al., A role for local inflammation in the formation of drusen in the aging eye. Am. J. Oplithalmol., 2002: 134:411-31.
Bok, D., Evidence for an inflammatory process in age-related macular degeneration gains new support. Proc. Natl. Acad. Sci. (USA). 2005: 102:7053-4.
Bora, et al., Role of Complement and Complement Membrane Attack Complex in Laser-Induced Choroidal Neovascularization. J. of Immunol. 2005, 174: 491-497.
Esparza-Gordillo, J., et al., Genetic and environmental factors influencing the human factor H plasma levels. Immunogenetics, 2004: 56:77-82.
Farries. T.C., et al., The mechanism of activation of the alternative pathway of complement by cell-bound C4b. Mol. Immunol., 27:1155-116 (1990).
Hageman, G.S., et al., An integrated hypothesis that considers drusen as biomarkers of immune-mediated processes at the RPE-Bruch's membrane interface in aging and age-related macular degeneration. Prog. Retin. Eye Res., 2001: 20:705-32.
Haines, J.L., et al., Complement factor H variant increases the risk of age-related macular degeneration. Science., 2005; 308:419-21.
Holers, V. M., In Clinical Immunology: Principles and Practice, ed. R. R. Rich. Mosby Press; 1996,363-391.
Johnson, L.V., et al., Complement activation and inflammatory processes in Drusen formation and age related macular degeneration. Exp. Eye Res., 2001: 73:887-96.
Krzystolik M. G., et al., Prevention of experimental choroidal neovascularization with intravitreal anti-vascular endothelial growth factor antibody fragment. Arch Ophthalm., 2002: 120:338-346.
Lesavre and H..J. Müller-Eberhard., Mechanism of action of factor D of the alternative complement pathway. J. Exp. Med., 1978; 148:1498-1510.
Rodriguez de Cordoba S., et al., The human complement factor H: functional roles, genetic variations and disease associations. Mol. Immunol., 2004; 41:355-67.
Volanakis, J. E., et al., Renal filtration and catabolism of complement protein D. New Eng . J. Med., 1985; 312:395-401.
Wang, Y., et al., Amelioration of lupus-like autoimmune disease in NZB/WF1 mice after treatment with a blocking monoclonal antibody specific for complement component C5. Proc. Natl. Acad. Sci.; 1996, 93:8563-8568.
Zareparsi, S., et al., Strong association of the Y402H variant in complement factor H at 1q32 with susceptibility to age-related macular degeneration. Am J Hum Genet. 2005; 77:149-53.
Bora et al., 2008, "The role of complement in ocular pathology." Semin Immunopathol. 30:85-95.
Diamond and Scharff, 1984, "Somatic mutation of the T15 heavy chain gives rise to an antibody with autoantibody specificity." Proc Natl Acad Sci U S A. 81(18):5841-4.
Fagerness et al., 2009, "Variation near complement factor I is associated with risk of advanced AMD." Eur J Hum Genet. 17:100-104.
Foote et al., 1992, "Antibody framework residues affecting the conformation of the hypervariable loops." J Mol Biol. 224(2):487-99.
Francis et al., 2009, "Polymorphisms in C2, CFB and C3 are associated with progression to advanced age related macular degeneration associated with visual loss." J Med Genet. 46:300-307.
Gold et al., 2006, "Variation in factor B (BF) and complement component 2 (C2) genes is associated with age-related macular degeneration." Nat Genet 38:458-462.

(56) References Cited

OTHER PUBLICATIONS

Heurich et al., 2011, "Common polymorphisms in C3, factor B, and factor H collaborate to determine systemic complement activity and disease risk." Proc Natl Acad Sci U S A. 108(20:8761-6.
Holers, 2008, "The spectrum of complement alternative pathway-mediated diseases." Immunol. Rev 223:300-316.
Kumagai and Tsumoto, 1998, "Generation of novel functional antibody molecules by in vitro selection system". Tanpakushitsu Kakusan Koso (Protein Nucleic Acid and Enzyme). 43(2):159-67. Review. In Japanese with English translation of an office action which indicates the degree of relevance (MPEP § 609.04(a) Eighth Edition, Revision 9, Aug. 2012), in particular that it is considered to be "related art" by the foreign office.
Loyet et al., 2010, "Anti-factor D Fab Specifically Inhibits the Alternative Complement Pathway: in vitro characterization and in vivo effects following administration to *cynomolgus* monkeys." AAPS J. v12 s1 (Abstract).
Mullins et al., 2000, "Drusen associated with aging and age-related macular degeneration contain proteins common to extracellular deposits associated with atherosclerosis, elastosis, amyloidosis, and dense deposit disease." FASEB J. 14:835-846.
Ohno et al., 1985, "Antigen-binding specificities of antibodies are primarily determined by seven residues of VH." Proc. Natl. Acad. Sci. 82:2945-2949.
Reynolds et al. 2009, "Plasma complement components and activation fragments: associations with age-related macular degeneration genotypes and phenotypes." Invest Ophthalmol Vis Sci. 50:5818-5827.
Roit et al., 2000, "Antibodies and cell receptors for antibodies." Immunology pp. 110-111 , pub. Mir, 2000 (in Russian with partial English translation).
Roversi et al., 2011, "Structural basis for complement factor I control and its disease-associated sequence polymorphisms."Proc Natl Acad Sci U S A. 108(31):12839-44.
Scholl et al. 2008, "Systemic complement activation in age-related macular degene a ion." PLoS One 3:e2593.
Tamura et al., 2000, "Structural correlates of an anticarcinoma antibody: identification of specificity-determining residues (SDRs) and development of a minimally immunogenic antibody variant by retention of SDRs only." J Immunol. 164(3):1432-41.
Undar et al., 2002, "Novel anti-factor D monoclonal antibody inhibits complement and leukocyte activation in a baboon model of cardiopulmonary bypass." Ann Thorac. Surg. 74(2):355-62.
Yates et al. 2007, "Complement C3 variant and the risk of age-related macular degeneration." N Engl J Med. 357:553-561.
Notice of Allowance, dated Jun. 20,2013 in U.S. Appl. No. 13/591,755 now published as U.S. Pat. Pub. 2012/0328613.

* cited by examiner

USE OF COMPLEMENT INHIBITORS TO TREAT OCULAR DISEASES

This application is a National Stage application of International Application No. PCT/US2006/043103, filed Nov. 4, 2006, which claims the benefit of U.S. Provisional Application No. 60/733,763 filed Nov. 4, 2005, the disclosure of each of which is incorporated by reference herein in their entireties.

FIELD OF THE INVENTION

This invention relates to the inhibition of the complement pathway, particularly Factor D, in patients suffering from ocular related conditions and diseases associated with complement activation such as age-related macular degeneration, diabetic retinopathy.

BACKGROUND OF THE INVENTION

Macular degeneration is a clinical term that is used to describe a family of diseases that are characterized by a progressive loss of central vision associated with abnormalities of the Bruch's membrane, the choroid, the neural retina and/or the retinal pigment epithelium. In the center of the retina is the macula lutea, which is about ⅓ to ½ cm. in diameter. The macula provides detailed vision, particularly in the center (the fovea), because the cones are higher in density. Blood vessels, ganglion cells, inner nuclear layer and cells, and the plexiform layers are all displaced to one side (rather than resting above the ones), thereby allowing light a more direct path to the cones. Under the retina is the choroid, a collection of blood vessels embedded within a fibrous tissue, and the pigmented epithelium (PE), which overlays the choroid layer. The choroidal blood vessels provide nutrition to the retina (particularly its visual cells). The choroid and PE are found at the posterior of the eye.

The retinal pigment epithelial (RPE) cells, which make up the PE, produce, store and transport a variety of factors that are responsible for the normal function and survival of photoreceptors. These multifunctional cells transport metabolites to the photoreceptors from their blood supply, the chorio capillaris of the eye. RPE cells also function as macrophages, phagocytizing the tips of the outer segments of rods and cones, which are produced in the normal course of cell physiology. Various ions, proteins and water move between the RPE cells and the interphotoreceptor space, and these molecules ultimately effect the metabolism and viability of the photoreceptors.

Age-related macular degeneration (AMD), the most prevalent macular degeneration, is associated with progressive loss of visual acuity in the central portion of the visual field, changes in color vision, and abnormal dark adaptation and sensitivity. Two principal clinical manifestations of AMD have been described as the dry, or atrophic, form, and the wet, or exudative, form. The dry form is associated with atrophic cell death of the central retina or macula, which is required for fine vision used for activities such as reading, driving or recognizing faces. About 10-20% of these dry AMD patients progress to the second form of AMD, known as wet AMD.

Wet (neovascular/exudative) AMD is caused by abnormal growth of blood vessels behind the retina under the macula and vascular leakage, resulting in displacement of the retina, hemorrhage and scar formation. This results in a deterioration of sight over a period of months to years. However, patients can suffer a rapid loss of vision. All wet AMD cases are originated from advanced dry AMD. The wet form accounts for 85% of blindness due to AMD. In wet AMD, as the blood vessels leak fluid and blood, scar tissue is formed that destroys the central retina.

The most significant risk factors for the development of both forms are age and the deposition of drusen, abnormal extracellular deposits, behind the retinal pigment epithelium. Drusen causes a lateral stretching of the RPE monolayer and physical displacement of the RPE from its immediate vascular supply, the choriocapillaris. This displacement creates a physical barrier that may impede normal metabolite and waste diffusion between the choriocapillaris and the retina. Drusen are the hallmark deposits associated with AMD. The biogenesis of drusen involves RPE dysfunction, impaired digestion of photoreceptor outer segments, and subsequent debris accumulation. Drusen contain complement activators, inhibitors, activation-specific complement fragments, and terminal pathway components, including the membrane attack complex (MAC or C5b-9), which suggests that focal concentration of these materials may produce a powerful chemotactic stimulus for leukocytes acting via a complement cascade (Killingsworth, et al., (2001) Exp Eye Res 73, 887-96). Recent studies have implicated local inflammation and activation of the complement cascade in their formation (Bok D. Proc Natl Acad Sci (USA). 2005; 102: 7053-4; Hageman G S, et al. Prog Retin Eye Res. 2001; 20: 705-32; Anderson D H, et al. Am J Ophthalmol. 2002; 134: 411-31. Johnson L V, et al. Exp Eye Res. 2001; 73: 887-96).

Wet AMD is associated with choroidal neovascularization (CNV) and is a complex biological process. Pathogenesis of new choroidal vessel formation is poorly understood, but such factors as inflammation, ischemia, and local production of angiogenic factors are thought to be important. Although inflammation has been suggested as a playing a role, the role of complement has not been explored. A preliminary study of CNV has been shown to be caused by complement activation in a mouse model (Bora P S, J Immunol. 2005; 174: 491-497).

The complement system is a crucial component of the innate immunity against microbial infection and comprises a group of proteins that are normally present in the serum in an inactive state. These proteins are organized in three activation pathways: the classical, the lectin, and the alternative pathways (V. M. Holers, In Clinical Immunology: Principles and Practice, ed. R. R. Rich, Mosby Press; 1996, 363-391). Molecules on the surface of microbes can activate these pathways resulting in the formation of protease complexes known as C3-convertases. The classical pathway is a calcium/magnesium-dependent cascade, which is normally activated by the formation of antigen-antibody complexes. It can also be activated in an antibody-independent manner by the binding of C-reactive protein complexed with ligand and by many pathogens including gram-negative bacteria. The alternative pathway is a magnesium-dependent cascade which is activated by deposition and activation of C3 on certain susceptible surfaces (e.g. cell wall polysaccharides of yeast and bacteria, and certain biopolymer materials).

The alternative pathway participates in the amplification of the activity of both the classical pathway and the lectin pathway (Suankratay, C., ibid; Farries, T. C. et al., Mol. Immunol. 27: 1155-1161(1990)). Activation of the complement pathway generates biologically active fragments of complement proteins, e.g. C3a, C4a and C5a anaphylatoxins and C5b-9 membrane attack complexes (MAC), which mediate inflammatory responses through involvement of leukocyte chemotaxis, activation of macrophages, neutrophils, platelets, mast cells and endothelial cells, increased vascular permeability, cytolysis, and tissue injury.

Factor D may be a suitable target for the inhibition of this amplification of the complement pathways because its plasma concentration in humans is very low (1.8 µg/ml), and it has been shown to be the limiting enzyme for activation of the alternative complement pathway (P. H. Lesavre and H. J. Müller-Eberhard. J. Exp. Med., 1978; 148: 1498-1510; J. E. Volanakis et al., New Eng. J. Med., 1985; 312: 395-401). The inhibition of complement activation has been demonstrated to be effective in treating several disease indications using animal models and in ex vivo studies, e.g. systemic lupus erythematosus and glomerulonephritis (Y. Wang et al., Proc. Natl. Acad. Sci.; 1996, 93: 8563-8568).

Using single-nucleotide polymorphism (SNP) analysis of AMD patients, a Factor H genetic variant (Y402H) was found to be highly associated with increased incidence of AMD (Zareparsi S, Branham K E H, Li M, et al. Am J Hum Genet. 2005; 77: 149-53; Haines J L, et al. Sci 2005; 208: 419-21). Persons who are either homozygous or heterozygous for this point mutation of Factor H gene may account for 50% of AMD cases. Factor H is the key soluble inhibitor of the alternative complement pathway (Rodriguez de Cordoba S, et al. Mol Immunol 2004; 41: 355-67). It binds to C3b and thus accelerates the decay of the alternative pathway C3-convertase (C3bBb) and acts as a co-factor for the Factor I-mediated proteolytic inactivation of C3b. Histochemical staining studies show that there is similar distribution of Factor H and MAC at the RPE-choroid interface. Significant amounts of deposited MAC at this interface found in AMD patients indicate that the Factor H haplotype (Y402H) may have attenuated complement inhibitory function. It is speculated that Factor H (Y402H) may have a lower binding affinity for C3b. Therefore, it is not as effective as wild type Factor H in inhibiting the activation of the alternative complement pathway. This puts RPE and choroids cells at sustained risk for alternative pathway-mediated complement attack.

It had been shown that lack of Factor H in plasma causes uncontrolled activation of the alternative pathway with consumption of C3 and often other terminal complement components such as C5. In keeping with this finding, plasma levels of Factor H are known to decrease with smoking, a known risk Factor for AMD (Esparza-Gordillo J, et al. Immunogenetics. 2004; 56: 77-82).

Currently, there is no proven medical therapy for dry AMD, and no treatments available for advanced dry AMD. In selected cases of wet AMD, a technique known as laser photocoagulation may be effective for sealing leaky or bleeding blood vessels. Unfortunately, laser photocoagulation usually does not restore lost vision, but merely slows, and in some cases, prevents further loss. Recently, photodynamic therapy has shown to be effective in stopping abnormal blood vessel growth in about one third of wet AMD patients when treated early. In Visdyne Photodynamic Therapy (PDT), a dye is injected into the patient's eye, it accumulates in the area of vessel leakage in the retina and, when exposed to a low power laser, it reacts sealing off the leaking vessels. In addition to these two laser techniques, there are several anti-angiogenesis therapies targeting vascular endothelial growth Factor (VEGF) being developed for the treatment of wet AMD. However, only 10% treated patients show vision improvement.

In view of these inadequate treatments for wet AMD and the total lack of treatments available for advanced dry AMD, there is a clear need for the development of new treatments for this serious disease. Our invention provides a novel approach to treating this serious disease.

SUMMARY OF THE INVENTION

The present invention relates to complement inhibitors for the treatment of ocular related conditions or diseases, such as age-related macular degeneration (AMD), diabetic retinopathy, ocular angiogenesis (such as ocular neovascularization affecting choroidal, corneal, or retinal tissue), and other ocular conditions involving complement activation. Treatment of AMD includes both the dry and wet forms of AMD.

The complement inhibitors of the present invention include, but are not limited to, those inhibiting the alternative complement pathway, such as Factor D, properdin, Factor B, Factor Ba, and Factor Bb, and the classical complement pathway, such as C3a, C5, C5a, C5b, C6, C7, C8, C9 and C5b-9. The present invention also includes the use of complement inhibitors in combination with other agents, such as anti-angiogenic agents and anti-inflammatory agents such as steroids.

Another embodiment of the present invention relates to the use of C5aR and C3aR inhibitors, such as antibodies and derived fragments and single domain constructs, as well as small molecule compounds.

Another embodiment of the present invention relates to the use of recombinant soluble CR1 (TP10) and its derived proteins; use of C3 inhibiting molecules (such as Compstatin, a peptidomimetic that binds and inhibits C3 activation); siRNAs that block the synthesis of C3, C5, FD, factor P, factor B These inhibitors can be, but not limited to, small molecule chemical compounds, nucleotides, peptides, proteins, peptidomimetics and antibodies.

Another embodiment of the present invention includes the use of human Factor H purified from human blood or recombinant human Factor H administered to patients intraocularly or by any other clinically effective route.

Antibodies of the present invention include whole immunoglobulins, scFv, Fab, Fab', Fv, F(ab')2, or dAb. Domain antibodies comprise either a VH domain or a VL domain.

One embodiment of the present invention is the use of a monoclonal antibody which binds to Factor D and blocks its ability to activate the alternative complement pathway. Such antibodies are described in WO 01170818 and US 20020081293, which are incorporated here by reference, such as monoclonal antibody 166-32 produced from the hybridoma deposited with the American Type Culture Collection (ATCC), 12301 Parklawn Drive, Rockville, Md. 20852, U.S., on Feb. 24, 1998, and designated HB12476. The present invention also includes antibodies that specifically bind to the same epitope as monoclonal antibody 166-32. Monoclonal antibodies of the present invention may also include the humanized antibodies of co-pending application Ser. No. 60/856,505 filed Nov. 2, 2006, which is incorporated herein by reference.

One embodiment of the present invention is the use of a monoclonal antibody which binds to complement component C5a. Such antibodies include antibody 137-26 produced from the hybridoma deposited with the ATCC and designated PTA-3650, and any antibody that specifically binds to the same epitope as 137-26.

According to the present invention, the complement pathway inhibitor may be administered by (a) parenteral administration; (b) biocompatible or bioerodable sustained release implant; (c) implantation of an infusion pump; or (d) local administration, such as subconjunctival administration or by intravitreal administration. The complement inhibitor may also be administered by parenteral administration selected from oral administration, enteral administration and topical administration. Topical administration may include an eye wash solution, an eye ointment, an eye shield or an eye drop solution.

In addition the complement inhibitor of the present invention may be administered in combination with a immunomodulatory or immunosuppressive compound.

Another embodiment of the present invention relates to the administration of nucleic acid constructs that are capable of expressing the complement pathway inhibitors for gene therapy.

Another embodiment of the present invention includes a method for screening for complement inhibitors that are useful in the treatment of AMD comprising the use of an AMD model in senescent Cc1-2 or Ccr-2-deficient mice. These mice manifest similar histopathological changes found in human dry and wet AMDs. These mice may be treated with complement inhibitors or Factor H intravitreally. Histological examination may be performed to determine protection from AMD development in mice treated with the agents to be tested.

DETAILED DESCRIPTION OF THE INVENTION

This invention is not limited to the particular methodology, protocols, cell lines, vectors, or reagents described herein because they may vary. Further, the terminology used herein is for the purpose of describing particular embodiments only and is not intended to limit the scope of the present invention. As used herein and in the appended claims, the singular forms "a", "an", and "the" include plural reference unless the context clearly dictates otherwise, e.g., reference to "a host cell" includes a plurality of such host cells.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the exemplary methods, devices, and materials are described herein.

All patents and publications mentioned herein are incorporated herein by reference to the extent allowed by law for the purpose of describing and disclosing the proteins, enzymes, vectors, host cells, and methodologies reported therein that might be used with the present invention. However, nothing herein is to be construed as an admission that the invention is not entitled to antedate such disclosure by virtue of prior invention.

Definitions

The term "amino acid sequence variant" refers to polypeptides having amino acid sequences that differ to some extent from a native sequence polypeptide. Ordinarily, amino acid sequence variants will possess at least about 70% homology, or at least about 80%, or at least about 90% homology to the native polypeptide. The amino acid sequence variants possess substitutions, deletions, and/or insertions at certain positions within the amino acid sequence of the native amino acid sequence.

The term "identity" or "homology" is defined as the percentage of amino acid residues in the candidate sequence that are identical with the residue of a corresponding sequence to which it is compared, after aligning the sequences and introducing gaps, if necessary to achieve the maximum percent identity for the entire sequence, and not considering any conservative substitutions as part of the sequence identity. Neither N- or C-terminal extensions nor insertions shall be construed as reducing identity or homology. Methods and computer programs for the alignment are well known in the art. Sequence identity can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, 30 H., and Lipman, D., SIAM J. Applied Math., 48: 1073 (1988). Methods to determine identity are designed to give the largest match between the sequences tested. Computer program methods to determine identity between two sequences include, but are not limited to, the GCG program package (Devereux, J., et al., Nucleic Acids Research 12(1): 387 (1984)), BLASTP, BLASTN, and FASTA (Atschul, S. F. et al., J Molec. Biol. 215: 403-410 (1990). The BLAST X program is publicly available from NCBI and other sources (BLASTManual, Altschul, S., et al, NCBI NLM NIH Bethesda, Md. 20894, Altschul, S., et al., J. Mol. Biol. 215: 403-410 (1990). The well-known Smith Waterman algorithm may also be used to determine identity.

The term "antibody" herein is used in the broadest sense and specifically covers intact monoclonal antibodies, polyclonal antibodies, multispecific antibodies (e.g. bispecific antibodies) formed from at least two intact antibodies, and antibody fragments, so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. In contrast to polyclonal antibody preparations which include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al, *Nature,* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature,* 352:624-628 (1991) and Marks et al., *J. Mol. Biol.,* 222:581-597 (1991), for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al, *Proc. Natl. Acad. Sci. USA,* 81:6851-6855 (1984)).

"Antibody fragments" comprise a portion of an intact antibody comprising the antigen-binding or variable region thereof. Examples of antibody fragments include Fab, Fab', F(ab')$_2$, and Fv fragments; diabodies; linear antibodies; single-chain antibody molecules; and multispecific antibodies formed from antibody fragment(s).

An "intact" antibody is one which comprises an antigen-binding variable region as well as a light chain constant domain ($C_L$) and heavy chain constant domains, $C_H1$, $C_H2$ and $C_H3$. The constant domains may be native sequence constant domains (e.g. human native sequence constant domains) or amino acid sequence variant thereof. The intact antibody may have one or more effector functions.

Antibody "effector functions" refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc.

Depending on the amino acid sequence of the constant domain of their heavy chains, intact antibodies can be assigned to different "classes". There are five-major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

"Antibody-dependent cell-mediated cytotoxicity" (ADCC) refers to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells. To assess ADCC activity of a molecule of interest, an in vitro ADCC assay, such as that described in U.S. Pat. Nos. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model. Several such models are available.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. These hypervariable regions are also called complementarity determining regions or CDRs. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)).

The term "hypervariable region" when used herein refers to the amino acid residues of an antibody which are responsible for antigen-binding. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (e.g. residues 2632 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-binding sites and is still capable of cross-linking antigen.

The Fab fragment also contains the constant domain of the light chain and the first constant domain (CH I) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa (κ) and lambda (λ), based on the amino acid sequences of their constant domains.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the scFv to form the desired structure for antigen binding. For a review of scFv see Plückthun in *The Pharmacology of Monoclonal Antibodies*, vol. 113, Rosenburg and Moore eds., Springer-Verlag, New York, pp. 269-315 (1994). Anti-ErbB2 antibody scFv fragments are described in WO93/16185; U.S. Pat. Nos. 5,571,894; and 5,587,458.

The term "diabodies" refers to small antibody fragments with two antigen-binding sites, which comprise a variable heavy domain ($V_H$) connected to a variable light domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

A "single-domain antibody" is synonymous with "dAb" and refers to an immunoglobulin variable region polypeptide wherein antigen binding is effected by a single variable region domain. A "single-domain antibody" as used herein, includes i) an antibody comprising heavy chain variable domain (VH), or antigen binding fragment thereof, which forms an antigen binding site independently of any other variable domain, ii) an antibody comprising a light chain variable domain (VL), or antigen binding fragment thereof, which forms an antigen binding site independently of any other variable domain, iii) an antibody comprising a VH domain polypeptide linked to another VH or a VL domain polypeptide (e.g., VH-VH or VHx-VL), wherein each V domain forms an antigen binding site independently of any other variable domain, and iv) an antibody comprising VL domain polypeptide linked to another VL domain polypeptide (VL-VL), wherein each V domain forms an antigen binding site independently of any other variable domain. As used herein, the VL domain refers to both the kappa and lambda forms of the light chains.

"Humanized" forms of non-human (e.g., rodent) antibodies are chimeric antibodies that contain minimal sequence derived from non-human immunoglobulin. Humanized antibodies are human immunoglobulins wherein the hypervariable regions are replaced by residues from a hypervariable region of a non-human species, such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the human antibody or in the non-human antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Examples of humanization technology may be found in, e.g., Queen et al. U.S. Pat. Nos. 5,585,089, 5,693,761; 5,693,762; and 6,180,370, which are incorporated herein by reference.

Antibody Generation

The antibodies of the present invention may be generated by any suitable method known in the art. The antibodies of the present invention may comprise polyclonal antibodies. Methods of preparing polyclonal antibodies are known to the skilled artisan (Harlow, et al., Antibodies: a Laboratory Manual, (Cold spring Harbor Laboratory Press, 2nd ed. (1988), which is hereby incorporated herein by reference in its entirety).

For example, antibodies may be generated by administering an immunogen comprising the antigen of interest to various host animals including, but not limited to, rabbits, mice, rats, etc., to induce the production of sera containing polyclonal antibodies specific for the antigen. The administration of the immunogen may entail one or more injections of an immunizing agent and, if desired, an adjuvant. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Additional examples of adjuvants which may be employed include the MPL-TDM adjuvant (monophosphoryl lipid A, synthetic trehalose dicorynomycolate). Immunization protocols are well known in the art in the art and may be performed by any method that elicits an immune response in the animal host chosen. Adjuvants are also well known in the art.

Typically, the immunogen (with or without adjuvant) is injected into the mammal by multiple subcutaneous or intraperitoneal injections, or intramuscularly or through IV. The immunogen may include an antigenic polypeptide, a fusion protein or variants thereof. Depending upon the nature of the polypeptides (i.e., percent hydrophobicity, percent hydrophilicity, stability, net charge, isoelectric point etc.), it may be useful to conjugate the immunogen to a protein known to be immunogenic in the mammal being immunized. Such conjugation includes either chemical conjugation by derivatizing active chemical functional groups to both the immunogen and the immunogenic protein to be conjugated such that a covalent bond is formed, or through fusion-protein based methodology, or other methods known to the skilled artisan. Examples of such immunogenic proteins include, but are not limited to, keyhole limpet hemocyanin, ovalbumin, serum albumin, bovine thyroglobulin, soybean trypsin inhibitor, and promiscuous T helper peptides. Various adjuvants may be used to increase the immunological response as described above.

The antibodies useful in the present invention comprise monoclonal antibodies. Monoclonal antibodies may be prepared using hybridoma technology, such as those described by Kohler and Milstein, Nature, 256:495 (1975) and U.S. Pat. No. 4,376,110, by Harlow, et al., Antibodies: A Laboratory Manual, (Cold spring Harbor Laboratory Press, 2.sup.nd ed. (1988), by Hammerling, et al., Monoclonal Antibodies and T-Cell Hybridomas (Elsevier, N.Y., (1981)), or other methods known to the artisan. Other examples of methods which may be employed for producing monoclonal antibodies include, but are not limited to, the human B-cell hybridoma technique (Kosbor et al., 1983, Immunology Today 4:72; Cole et al., 1983, Proc. Natl. Acad. Sci. USA 80:2026-2030), and the EBV-hybridoma technique (Cole et al., 1985, Monoclonal Antibodies And Cancer Therapy, Alan R. Liss, Inc., pp. 77-96). Such antibodies may be of any immunoglobulin class including IgG, IgM, IgE, IgA, IgD and any subclass thereof. The hybridoma producing the antibodies of this invention may be cultivated in vitro or in vivo.

Using typical hybridoma techniques, a host such as a mouse, a humanized mouse, a mouse with a human immune system, hamster, rabbit, camel or any other appropriate host animal, is typically immunized with an immunogen to elicit lymphocytes that produce or are capable of producing antibodies that will specifically bind to the antigen of interest. Alternatively, lymphocytes may be immunized in vitro with the antigen.

Generally, in making antibody-producing hybridomas, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986), pp. 59-103). Immortalized cell lines are usually transformed mammalian cells, particularly myeloma cells of rodent, bovine or human origin. Typically, a rat or mouse myeloma cell line is employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), substances that prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines may also be used for the production of human monoclonal antibodies (Kozbor, J. Immunol., 133: 3001 (1984); Brodeur et al., Monoclonal Antibody Production Techniques and Applications, Marcel Dekker, Inc., New York, (1987) pp. 51-63).

The culture medium in which the hybridoma cells are cultured can then be assayed for the presence of monoclonal antibodies directed against the immunogen. The binding specificity of monoclonal antibodies produced by the hybridoma cells is determined by, e.g., immunoprecipitation or by an in vitro binding assay, such as radioimmunoassay (RIA) or enzyme-linked immunoadsorbant assay (ELISA). Such techniques are known in the art and within the skill of the artisan. The binding affinity of the monoclonal antibody can, for example, be determined by a Scatchard analysis (Munson et al., Anal. Biochem., 107:220 (1980)).

After the desired hybridoma cells are identified, the clones may be subcloned by limiting dilution procedures and grown by standard methods (Goding, supra). Suitable culture media for this purpose include, for example, Dulbecco's Modified Eagle's Medium and RPMI-1640. The monoclonal antibodies secreted by the subclones may be isolated or purified from the culture medium by conventional immunoglobulin purification procedures such as, e.g., protein A-sepharose, hydroxyapatite chromatography, gel exclusion chromatography, gel electrophoresis, dialysis, or affinity chromatography.

A variety of methods exist in the art for the production of monoclonal antibodies and thus, the invention is not limited to their sole production in hybridomas. For example, the monoclonal antibodies may be made by recombinant DNA methods, such as those described in U.S. Pat. No. 4,816,567. In this context, the term "monoclonal antibody" refers to an antibody derived from a single eukaryotic, phage, or prokaryotic clone. The DNA encoding the monoclonal antibodies of the invention can be readily isolated and sequenced using conventional procedures (e.g., by using oligonucleotide probes that are capable of binding specifically to genes encoding the heavy and light chains of murine antibodies, or such chains from human, humanized, or other sources). The hydridoma cells of the invention serve as a preferred source of such DNA. Once isolated, the DNA may be placed into expression vectors, which are then transformed into host cells such as NS0 cells, Simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison et al, supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain cross-linking. Alternatively, the relevant cysteine residues are substituted with another amino acid residue or are deleted so as to prevent cross-linking.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191-202; U.S. Pat. Nos. 5,807,715; 4,816,567; and 4,816397, which are incorporated herein by reference in their entirety.

Humanized antibodies are antibody molecules generated in a non-human species that bind the desired antigen having one or more complementarity determining regions (CDRs) from the non-human species and framework (FR) regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties). Antibodies can be humanized using a variety of techniques known in the art including, for example, CDR-grafting (EP 239,400; PCT publication WO 91/09967; U.S. Pat. Nos. 5,225,539; 5,530,101; and 5,585, 089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332).

Generally, a humanized antibody has one or more amino acid residues introduced into it from a source that is non-human. These non-human amino acid residues are often referred to as "import" residues, which are typically taken from an "import" variable domain. Humanization can be essentially performed following the methods of Winter and co-workers (Jones et al., Nature, 321:522-525 (1986); Reichmann et al., Nature, 332:323-327 (1988); Verhoeyen et al., Science, 239:1534-1536 (1988), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possible some FR residues are substituted from analogous sites in rodent antibodies.

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety. The techniques of Cole et al., and Boerder et al., are also available for the preparation of human monoclonal antibodies (Cole et al., Monoclonal Antibodies and Cancer Therapy, Alan R. Riss, (1985); and Boerner et al., J. Immunol., 147(1):86-95, (1991)).

Human antibodies can also be single-domain antibodies having a VH or VL domain that functions independently of any other variable domain. These antibodies are typically selected from antibody libraries expressed in phage. These antibodies and methods for isolating such antibodies are described in U.S. Pat. Nos. 6,595,142; 6,248,516; and applications US20040110941 and US20030130496 all of which are incorporated herein by reference.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.), Genpharm (San Jose, Calif.), and Medarex, Inc. (Princeton, N.J.) can be engaged to provide human antibodies directed against a selected antigen using technology similar to that described above.

Also human MAbs could be made by immunizing mice transplanted with human peripheral blood leukocytes, splenocytes or bone marrows (e.g., Trioma techniques of XTL). Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899-903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437-444; (1989) and Nissinoff, J. Immunol. 147(8):2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

The antibodies of the present invention may be bispecific antibodies. Bispecific antibodies are monoclonal, preferably human or humanized, antibodies that have binding specificities for at least two different antigens. In the present invention, one of the binding specificities may be directed towards Factor D, the other may be for any other antigen, and preferably for a cell-surface protein, receptor, receptor subunit, tissue-specific antigen, virally derived protein, virally encoded envelope protein, bacterially derived protein, or bacterial surface protein, etc. Bispecific antibodies may also comprise two or more single-domain antibodies.

Methods for making bispecific antibodies are well known. Traditionally, the recombinant production of bispecific antibodies is based on the co-expression of two immunoglobulin heavy-chain/light-chain pairs, where the two heavy chains have different specificities (Milstein and Cuello, Nature, 305: 537-539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It may have the first heavy-chain constant region (CH1) containing the site necessary for light-chain binding present in at least one of the fusions. DNAs encoding the immunoglobulin heavy-chain fusions and, if desired, the immununoglobulin light chain, are inserted into separate expression vectors, and are co-transformed into a suitable host organism. For further details of generating bispecific antibodies see, for example Suresh et al., Meth. In Enzym., 121:210 (1986).

Heteroconjugate antibodies are also contemplated by the present invention. Heteroconjugate antibodies are composed of two covalently joined antibodies. Such antibodies have, for example, been proposed to target immune system cells to unwanted cells (U.S. Pat. No. 4,676,980). It is contemplated that the antibodies may be prepared in vitro using known methods in synthetic protein chemistry, including those involving cross-linking agents. For example, immunotoxins may be constructed using a disulfide exchange reaction or by forming a thioester bond. Examples of suitable reagents for this purpose include iminothiolate and methyl-4-mercaptobutyrimidate and those disclosed, for example, in U.S. Pat. No. 4,676,980. In addition, one can generate single-domain antibodies to IL-13. Examples of this technology have been described in WO9425591 for antibodies derived from Camelidae heavy chain Ig, as well in US20030130496 describing the isolation of single domain fully human antibodies from phage libraries.

Generation of Monoclonal Antibodies (MABS)

In one embodiment of the invention, monoclonal antibodies, such as anti-Factor D, can be raised by immunizing rodents (e.g. mice, rats, hamsters and guinea pigs) with either native Factor D purified from human plasma or urine, or recombinant Factor D or its fragments expressed by either eukaryotic or prokaryotic systems. Other animals can be used for immunization, e.g. non-human primates, transgenic mice expressing human immunoglobulins and severe combined immunodeficient (SCID) mice transplanted with human B lymphocytes. Hybridomas can be generated by conventional procedures by fusing B lymphocytes from the immunized animals with myeloma cells (e.g. Sp2/0 and NS0), as described by G. Köhler and C. Milstein (Nature, 1975: 256: 495-497).

In addition, monoclonal antibodies can be generated by screening of recombinant single-chain Fv or Fab libraries from human B lymphocytes in phage-display systems. The specificity of the MAbs to a given antigen can be tested by enzyme linked immunosorbent assay (ELISA), Western immunoblotting, or other immunochemical techniques. The inhibitory activity of the antibodies on complement activation can be assessed by hemolytic assays using unsensitized rabbit or guinea pig red blood cells (RBCs) for the alternative pathway, and using sensitized chicken or sheep RBCs for the classical pathway. The hybridomas in the positive wells are cloned by limiting dilution. The antibodies are purified for characterization for specificity to the antigen, such as Factor D, by the assays well known in the art.

One can also create single peptide chain binding molecules in which the heavy and light chain Fv regions are connected. Single chain antibodies ("ScFv") and the method of their construction are described in U.S. Pat. No. 4,946,778. Alternatively, Fab can be constructed and expressed by similar means (M. J. Evans et al., J. Immunol. Meth., 1995; 184: 123-138). All of the wholly and partially human antibodies are less immunogenic than wholly murine MAbs, and the fragments and single chain antibodies are also less immunogenic. All these types of antibodies are therefore less likely to evoke an immune or allergic response. Consequently, they are better suited for in vivo administration in humans than wholly animal antibodies, especially when repeated or long-term administration is necessary. In addition, the smaller size of the antibody fragment may help improve tissue bioavailability, which may be critical for better dose accumulation in acute disease indications.

In one preferred embodiment of the invention, a chimeric Fab, having animal (mouse) variable regions and human constant regions is used therapeutically. The Fab is preferred because it is smaller than a whole immunoglobulin and may provide better tissue permeation; as monovalent molecule, there is less chance of immunocomplexes and aggregates forming; and it can be produced in a microbial system, which can more easily be scaled-up than a mammalian system.

Applications of the Complement Pathway Inhibitors

The complement inhibitors, such as antibodies and their binding fragments, can be administered to subjects in an appropriate pharmaceutical formulation by a variety of routes, including, but not limited, intravenous infusion, intravenous bolus injection, and intraperitoneal, intradermal, intramuscular, subcutaneous, intranasal, intratracheal, intraspinal, intracranial, and oral routes. Such administration enables them to bind to endogenous antigen, such as Factor D and thus inhibit the generation of C3b, C3a and C5a anaphylatoxins, and C5b-9.

The estimated preferred dosage of such antibodies and molecules is between 10 and 500 µg/ml of serum. The actual dosage can be determined in clinical trials following the conventional methodology for determining optimal dosages, i.e., administering various dosages and determining which is most effective.

The complement pathway inhibitors can function to inhibit in vivo complement activation and/or the alternative complement pathway and inflammatory manifestations that accompany it, such as recruitment and activation of macrophages, neutrophils, platelets, and mast cells, edema, and tissue damage. These inhibitors can be used for treatment of diseases or conditions that are mediated by excessive or uncontrolled activation of the complement system.

The antibodies of the present invention may be monospecific, bispecific, trispecific or of greater multispecificity. Multispecific antibodies may be specific for different epitopes of a chosen antigen or may be specific for both the antigen as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601, 819; Kostelny et al., J. Immunol. 148:1547-1553 (1992).

Antibodies useful in the present invention may be described or specified in terms of the epitope(s) or portion(s) of a complement pathway component, such as Factor D, which they recognize or specifically bind. The epitope(s) or polypeptide portion(s) may be specified as described herein, e.g., by N-terminal and C-terminal positions, by size in contiguous amino acid residues.

Antibodies useful in the present invention may also be described or specified in terms of their cross-reactivity. Antibodies that bind complement pathway component polypeptides, which have at least 95%, at least 90%, at least 85%, at least 80%, at least 75%, at least 70%, at least 65%, at least 60%, at least 55%, and at least 50% identity (as calculated using methods known in the art and described herein) to IL-13 are also included in the present invention. Anti-Factor D antibodies may also bind with a KD of less than about 10-7 M, less than about 10-6 M, or less than about 10-5 M to other proteins, such as Factor D antibodies from species other than that against which the anti-Factor D antibody is directed.

Vectors and Host Cells

In another aspect, the present invention provides vector constructs comprising a nucleotide sequence encoding the antibodies of the present invention and a host cell comprising such a vector. Standard techniques for cloning and transformation may be used in the preparation of cell lines expressing the antibodies of the present invention.

Recombinant expression vectors containing a nucleotide sequence encoding the antibodies of the present invention can be prepared using well known techniques. The expression vectors include a nucleotide sequence operably linked to suitable transcriptional or translational regulatory nucleotide sequences such as those derived from mammalian, microbial, viral, or insect genes. Examples of regulatory sequences include transcriptional promoters, operators, enhancers, MRNA ribosomal binding sites, and/or other appropriate sequences which control transcription and translation initiation and termination. Nucleotide sequences are "operably linked" when the regulatory sequence functionally relates to the nucleotide sequence for the appropriate polypeptide. Thus, a promoter nucleotide sequence is operably linked to, e.g., the antibody heavy chain sequence if the promoter nucleotide sequence controls the transcription of the appropriate nucleotide sequence.

In addition, sequences encoding appropriate signal peptides that are not naturally associated with antibody heavy and/or light chain sequences can be incorporated into expression vectors. For example, a nucleotide sequence for a signal peptide (secretory leader) may be fused in-frame to the polypeptide sequence so that the antibody is secreted to the periplasmic space or into the medium. A signal peptide that is functional in the intended host cells enhances extracellular secretion of the appropriate antibody. The signal peptide may be cleaved from the polypeptide upon secretion of antibody from the cell. Examples of such secretory signals are well known and include, e.g., those described in U.S. Pat. Nos. 5,698,435, 5,698,417, and 6,204,023.

Host cells useful in the present invention include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., Baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

The vector may be a plasmid vector, a single or double-stranded phage vector, or a single or double-stranded RNA or DNA viral vector. Such vectors may be introduced into cells as polynucleotides by well known techniques for introducing DNA and RNA into cells. The vectors, in the case of phage and viral vectors also may be introduced into cells as packaged or encapsulated virus by well known techniques for infection and transduction. Viral vectors may be replication competent or replication defective. In the latter case, viral propagation generally will occur only in complementing host cells. Cell-free translation systems may also be employed to produce the protein using RNAs derived from the present DNA constructs. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

Prokaryotes useful as host cells in the present invention include gram negative or gram positive organisms such as *E. coli*, and *B. subtilis*. Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the pKK223-3 (Pharmacia Fine Chemicals, Uppsala, Sweden), pGEM1 (Promega Biotec, Madison, Wis., USA), and the pET (Novagen, Madison, Wis., USA) and pRSET (Invitrogen Corporation, Carlsbad, Calif., USA) series of vectors (Studier, F. W., J. Mol. Biol. 219: 37 (1991); Schoepfer, R. Gene 124: 83 (1993)). Promoter sequences commonly used for recombinant prokaryotic host cell expression vectors include T7, (Rosenberg, et al. Gene 56, 125-135 (1987)), β-lactamase (penicillinase), lactose promoter system (Chang et al., Nature 275:615, (1978); and Goeddel et al., Nature 281:544, (1979)), tryptophan (trp) promoter system (Goeddel et al., Nucl. Acids Res. 8:4057, (1980)), and tac promoter (Sambrook et al., 1990, Molecular Cloning, A Laboratory Manual, 2d Ed., Cold Spring Harbor Laboratory, Cold Spring Harbor, N.Y.)

Yeasts useful in the present invention include those from the genus Saccharomyces, Pichia, Actinomycetes and Kluyveromyces. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., J. Biol. Chem. 255:2073, (1980)) or other glycolytic enzymes (Holland et al., Biochem. 17:4900, (1978)) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Fleer et al., Gene, 107:285-195 (1991). Other suitable promoters and vectors for yeast and yeast transformation protocols are well known in the art. Yeast transformation protocols are well known. One such protocol is described by Hinnen et al., Proc. Natl. Acad. Sci., 75:1929 (1978). The Hinnen protocol selects for Trp+ transformants in a selective medium.

Mammalian or insect host cell culture systems may also be employed to express recombinant antibodies, e.g., Baculovirus systems for production of heterologous proteins. In an insect system, Autographa califomica nuclear polyhedrosis virus (AcNPV) may be used as a vector to express foreign genes. The virus grows in Spodoptera frugiperda cells. The antibody coding sequence may be cloned individually into non-essential regions (for example the polyhedrin gene) of the virus and placed under control of an AcNPV promoter (for example the polyhedrin promoter).

NS0 or Chinese hamster ovary (CHO) cells for mammalian expression of the antibodies of the present invention may be used. Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus (CMV). DNA sequences derived from the SV40 viral genome may be used to provide other genetic elements for expression of a structural gene sequence in a mammalian host cell, e.g., SV40 origin, early and late promoter, enhancer, splice, and polyadenylation sites. Viral early and late promoters are particularly useful because both are easily obtained from a viral genome as a fragment which may also contain a viral origin of replication. Exemplary expression vectors for use in mammalian host cells are commercially available.

Polynucleotides Encoding Antibodies

The invention further provides polynucleotides or nucleic acids, e.g., DNA, comprising a nucleotide sequence encoding an antibody of the invention and fragments thereof. Exemplary polynucleotides include those encoding antibody chains comprising one or more of the amino acid sequences described herein. The invention also encompasses polynucleotides that hybridize under stringent or lower stringency hybridization conditions to polynucleotides that encode an antibody of the present invention.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties ), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the CDRs by well known methods, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine MAb and a human immunoglobulin constant region, e.g., humanized antibodies.

Alternatively, techniques described for the production of single chain antibodies (U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in E. coli may also be used (Skerra et al., Science 242:1038-1041 (1988)).

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody or a fragment of the antibody. Once a polynucleotide encoding an antibody molecule has been obtained, the vector for the production of the antibody may be produced by recombinant DNA technology. An expression vector is constructed containing antibody coding sequences and appropriate transcriptional and translational control signals. These methods include, for example, in vitro recombinant DNA techniques, synthetic techniques, and in vivo genetic recombination.

The expression vector is transferred to a host cell by conventional techniques and the transfected cells are then cultured by conventional techniques to produce an antibody of the invention. In one aspect of the invention, vectors encoding both the heavy and light chains may be co-expressed in the host cell for expression of the entire immunoglobulin molecule, as detailed below.

A variety of host-expression vector systems may be utilized to express the antibody molecules of the invention as described above. Such host-expression systems represent vehicles by which the coding sequences of interest may be produced and subsequently purified, but also represent cells which may, when transformed or transfected with the appropriate nucleotide coding sequences, express an antibody molecule of the invention in situ. Bacterial cells such as E. coli, and eukaryotic cells are commonly used for the expression of a recombinant antibody molecule, especially for the expression of whole recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, COS, 293, 3T3, or myeloma cells.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk, hgprt or aprt-cells, respectively. Also, antimetabolite resistance can be used as the basis of selection for the following genes: dhfr, which confers resistance to methotrexate (Wigler et al., Proc. Natl. Acad. Sci., USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 (Wu and Wu, Biotherapy 3:87-95 (1991)); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, "The use of vectors based on gene amplification for the expression of cloned genes in mammalian cells" (DNA Cloning, Vol. 3. Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and size-exclusion chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide. Fused or conjugated antibodies of the present invention may be used for ease in purification. See e.g., Harbor et al., supra, and PCT publication WO 93/21232; EP 439,095; Naramura et al., Immunol. Lett. 39:91-99 (1994); U.S. Pat. No. 5,474,981; Gillies et al., Proc. Natl. Acad. Sci. 89:1428-1432 (1992); Fell et al., J. Immunol. 146:2446-2452(1991), which are incorporated by reference in their entireties.

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

Diagnostic Uses for Antibodies

The antibodies of the invention include derivatives that are modified, i.e., by the covalent attachment of any type of molecule to the antibody, such that covalent attachment does not interfere with binding to the antigen. For example, but not by way of limitation, the antibody derivatives include antibodies that have been modified, e.g., by biotinylation, HRP, or any other detectable moiety.

Antibodies of the present invention may be used, for example, but not limited to, to detect Factor D, including both in vitro and in vivo diagnostic methods. For example, the antibodies have use in immunoassays for qualitatively and quantitatively measuring levels of Factor D in biological samples obtained from the eyes of subjects suffering from ocular conditions or diseases. Typically immunoassays are described in, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays.

The present invention further encompasses the use of antibodies or fragments thereof conjugated to a diagnostic agent for the detection of the levels of complement pathway components in the eye of an affected individual. The antibodies can be used diagnostically to, for example, monitor the development or progression of an ocular condition or disease as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111In or 99Tc.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Labeled antibodies, and derivatives and analogs thereof, which specifically bind to Factor D can be used for diagnostic purposes to detect, diagnose, or monitor diseases, disorders, and/or conditions associated with the aberrant expression and/or activity of Factor D. The invention provides for the detection of aberrant expression of Factor D, comprising (a) assaying the expression of Factor D in cells or body fluid of an individual using one or more antibodies of the present invention specific to Factor D and (b) comparing the level of gene expression with a standard gene expression level, whereby an increase or decrease in the assayed Factor D expression level compared to the standard expression level is indicative of aberrant expression.

Antibodies may be used for detecting the presence and/or levels of Factor D in a sample, e.g., ocular fluid. The detecting method may comprise contacting the sample with an anti-Factor D antibody and determining the amount of antibody that is bound to the sample.

The invention provides a diagnostic assay for diagnosing a disorder, comprising (a) assaying the expression of Factor D in cells or body fluid of an individual using one or more antibodies of the present invention and (b) comparing the level of gene expression with a standard gene expression level, whereby an increase or decrease in the assayed gene expression level compared to the standard expression level is indicative of a particular disorder.

Antibodies of the invention can be used to assay protein levels in a biological sample using classical immunohistological methods known to those of skill in the art (e.g., see Jalkanen, et al., J. Cell. Biol. 101:976-985 (1985); Jalkanen, et al., J. Cell. Biol. 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine (125I, 121I), carbon (14C), sulfur (35S), tritium (3H), indium (112In), and technetium (99Tc); luminescent labels, such as luminol; and fluorescent labels, such as fluorescein and rhodamine, and biotin.

One aspect of the invention is the detection and diagnosis of a disease or disorder associated with complement activation in the eyes of a subject, preferably a mammal and most preferably a human. In one embodiment, diagnosis comprises: a) taking a sample from the eye of a patient; b) measuring the level of complement components, such as C3a or C3b or C5a. Background level can be determined by various methods including, comparing the amount of labeled molecule detected to a standard value previously determined for a particular system.

In an embodiment, monitoring of the disease or disorder is carried out by repeating the method for diagnosing the disease or disease, for example, one month after initial diagnosis, six months after initial diagnosis, one year after initial diagnosis, etc.

Therapeutic Uses of Complement Pathway Inhibitors

Complement pathway inhibitors may be administered to a subject suffering from an ocular disease such as age-related macular degeneration. An antibody, with or without a therapeutic moiety conjugated to it, can be used as a therapeutic. The present invention is directed to the use of complement pathway inhibitors, particularly antibodies, comprising administering said inhibitors to an animal, a mammal, or a human, for treating a ocular disease, disorder, or condition involving complement pathway activation. The animal or subject may be an animal in need of a particular treatment, such as an animal having been diagnosed with a particular disorder, e.g., one relating to complement. Antibodies directed against Factor D are useful for inhibiting the alternative complement pathway and thus inhibiting complement pathway related disorders or conditions. In particular, the present invention relates to the treatment of AMD, diabetic retinopathy, and choroidal neovascularization. For example, by administering a therapeutically acceptable dose of an antibody, or antibodies, of the present invention, or a cocktail of the present antibodies, or in combination with other molecules of varying sources, the effects of activation of complement pathway components may be reduced or eliminated in the treated mammal.

Therapeutic compounds of the invention include, but are not limited to, antibodies of the invention (including fragments, analogs and derivatives thereof as described herein) and nucleic acids encoding antibodies of the invention as described below (including fragments, analogs and derivatives thereof and anti-idiotypic antibodies as described herein). The antibodies of the invention can be used to treat, inhibit or prevent diseases, disorders or conditions associated with aberrant expression and/or activity of the complement pathway, particularly the alternative pathway, and particularly Factor D. The treatment and/or prevention of diseases, disorders, or conditions associated with aberrant expression and/or activity of Factor D includes, but is not limited to, alleviating at least one symptoms associated with those diseases, disorders or conditions. Antibodies of the invention may be provided in pharmaceutically acceptable compositions as known in the art or as described herein.

The amount of the antibody which will be effective in the treatment, inhibition and prevention of a disease or disorder associated with aberrant expression and/or activation of the complement pathway can be determined by standard clinical techniques. The antibody can be administered in treatment regimes consistent with the disease, e.g., a single or a few doses over one to several days to ameliorate a disease state or periodic doses over an extended time to prevent ocular diseases or conditions.

In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation. In a preferred aspect, the antibody is substantially purified (e.g., substantially free from substances that limit its effect or produce undesired side-effects).

Various delivery systems are known and can be used to administer an antibody of the present invention, including injection, e.g., encapsulation in liposomes, microparticles, microcapsules, recombinant cells capable of expressing the compound, receptor-mediated endocytosis (see, e.g., Wu et al., J. Biol. Chem. 262:4429-4432 (1987)), construction of a nucleic acid as part of a retroviral or other vector, etc.

The antibody can be administered to the mammal in any acceptable manner. Methods of introduction include but are not limited to intradermal, intramuscular, intraperitoneal, intravenous, subcutaneous, intranasal, epidural, inhalation and oral routes. However, for purpose of the present invention, the preferred route of administration is intraocular.

Administration can be systemic or local. In addition, it may be desirable to introduce the therapeutic antibodies or compositions of the invention into the central nervous system by any suitable route, including intraventricular and intrathecal injection; intraventricular injection may be facilitated by an intraventricular catheter, for example, attached to a reservoir, such as an Ommaya reservoir.

In another embodiment, the antibody can be delivered in a vesicle, in particular a liposome (see Langer, Science 249: 1527-1533 (1990); Treat et al., in Liposomes in the Therapy of Infectious Disease and Cancer, Lopez-Berestein and Fidler (eds.), Liss, N.Y., pp. 353-365 (1989); Lopez-Berestein, ibid., pp. 317-327; see generally ibid.).

In yet another embodiment, the antibody can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target.

The present invention also provides pharmaceutical compositions useful in the present method. Such compositions comprise a therapeutically effective amount of the antibody, and a physiologically acceptable carrier. In a specific embodiment, the term "physiologically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such physiological carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable carriers are described in "Remington's Pharmaceutical Sciences" by E. W. Martin. Such compositions will contain an effective amount of the antibody, preferably in purified form, together with a suitable amount of carrier so as to provide the form for proper administration to the patient. The formulation should suit the mode of administration.

In one embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

In addition, the antibodies of the present invention may be conjugated to various effector molecules such as heterologous polypeptides, drugs, radionucleotides, or toxins. See, e.g., PCT publications WO 92/08495; WO 91/14438; WO 89/12624; U.S. Pat. No. 5,314,995; and EP 396,387. An antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologues thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dicliliorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immumunol. Rev. 62:119-58 (1982). Alternatively, an antibody can be conjugated to a second antibody to form an antibody heteroconjugate. (See, e.g., Segal in U.S. Pat. No. 4,676,980.)

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis Factor, α-interferon, β-interferon, nerve growth Factor, platelet derived growth Factor, tissue plasminogen activator, an apoptotic agent, e.g., TNF-α, TNF-β, AIM I (See, International Publication No. WO 97/33899), AIM II (See, International Publication No. WO 97/34911), Fas Ligand (Takahashi et al., Int. Immunol., 6:1567-1574(1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating Factor ("GM-CSF"), granulocyte colony stimulating Factor ("G-CSF"), or other growth Factors.

Antibody-Based Gene Therapy

In a another aspect of the invention, nucleic acids comprising sequences encoding antibodies or binding fragments thereof, are administered to treat, inhibit or prevent a disease or disorder associated with aberrant expression and/or activation of the complement pathway by way of gene therapy. Gene therapy refers to therapy performed by the administration to a subject of an expressed or expressible nucleic acid. In this embodiment of the invention, the nucleic acids produce their encoded protein that mediates a therapeutic effect. Any of the methods for gene therapy available can be used according to the present invention. Exemplary methods are described below.

For general reviews of the methods of gene therapy, see Goldspiel et al., Clinical Pharmacy 12:488-505 (1993); Wu and Wu, Biotherapy3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993).

In a one aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific.

In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijistra et al., Nature 342:435-438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contain nucleic acid sequences encoding an antibody of the invention are used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates the delivery of the gene into a patient. More detail about retroviral vectors can be found in Boesen et al., Biotherapy 6:291-302 (1994), which describes the use of a retroviral vector to deliver the mdrl gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. Gen. and Dev. 3:110-114 (1993).

Adenoviruses may also be used in the present invention. Adenoviruses are especially attractive vehicles in the present invention for delivering antibodies to respiratory epithelia. Adenoviruses naturally infect respiratory epithelia. Other targets for adenovirus-based delivery systems are liver, the central nervous system, endothelial cells, and muscle. Adenoviruses have the advantage of being capable of infecting non-dividing cells. Kozarsky and Wilson, Curr. Opin. Gen. Dev. 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). Adeno-associated virus (AAV) has also been proposed for use in gene therapy (Walsh et al., Proc. Soc. Exp. Biol. Med. 204:289-300 (1993); U.S. Pat. Nos. 5,436,146; 6,632,670; 6,642,051).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599-618 (1993); Cohen et al., Meth. Enzymol. 217:618-644 (1993); Cline, Pharmac. Ther. 29:69-92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a one embodiment, the cell used for gene therapy is autologous to the patient. Nucleic acid sequences encoding an antibody of the present invention are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973-985 (1992); Rheinwald, Meth. Cell Bio. 21A:229 (1980); and Pittelkow and Scott, Mayo Clinic Proc. 61:771 (1986)).

Modulating Complement Pathway Component Expression By SIRNA siRNAs have proven useful as a tool in studies of modulating gene expression where traditional antagonists such as small molecules or antibodies may be less effective. (Shi Y., Trends in Genetics 19(1):9-12 (2003)). In vitro synthesized, double stranded RNAs that are 21 to 23 nucleotides in length can act as interfering RNAs (iRNAs) and can specifically inhibit gene expression (Fire A., Trends in Genetics 391; 806-810 (1999)). These iRNAs act by mediating degradation of their target RNAs. Since they are under 30 nucleotides in length, they do not trigger a cell antiviral defense mechanism. Such mechanisms include interferon production, and a general shutdown of host cell protein synthesis. Practically, siRNAs can by synthesized and then cloned into DNA vectors. Such vectors can be transfected and made to express the siRNA at high levels. The high level of siRNA expression is used to "knockdown" or significantly reduce the amount of protein produced in a cell, and thus it is useful in experiments where overexpression of a protein is believed to be linked to a disorder such as cancer. siRNAs are useful antagonists to complement pathway proteins by limiting cellular production of the antigen and inhibit activation of the complement cascade.

Peptidomimetics and Small Molecules

It is well-known to those normally skilled in the art that it is possible to replace peptides with peptidomimetics. Peptidomimetics are generally preferable as therapeutic agents to peptides owing to their enhanced bioavailability and relative lack of attack from proteolytic enzymes. Techniques of molecular modeling may be used to design a peptidomimetics which mimic the structure of the complement related peptides disclosed herein. Accordingly, the present invention also provides peptidomimetics and other lead compounds which can be identified based on the data obtained from structural analysis of the complement pathway protein. A potential Factor D analog may be examined through the use of computer modeling using a docking program such as GRAM, DOCK, or AUTODOCK. This procedure can include computer fitting of potential Factor D analogs. Computer programs can also be employed to estimate the attraction, repulsion, and steric hindrance of an analog to a potential binding site. Generally the tighter the fit (e.g., the lower the steric hindrance, and/or the greater the attractive force) the more potent the potential drug will be since these properties are consistent with a tighter binding constant. Furthermore, the more specificity in the design of a potential drug the more likely that the drug will not interfere with other properties of the expression system. This will minimize potential side-effects due to unwanted interactions with other proteins.

Initially a potential Factor D analog could be obtained by screening a random peptide library produced by a recombinant bacteriophage, for example, or a chemical library. An analog ligand selected in this manner could be then be systematically modified by computer modeling programs until one or more promising potential ligands are identified.

Such computer modeling allows the selection of a finite number of rational chemical modifications, as opposed to the countless number of essentially random chemical modifications that could be made, and of which any one might lead to a useful drug. Thus through the use of the three-dimensional structure disclosed herein and computer modeling, a large number of compounds is rapidly screened and a few likely candidates can be determined without the laborious synthesis of untold numbers of compounds.

Once a potential Factor D analog is identified it can be either selected from a library of chemicals commercially available from most large chemical companies including Merck, Glaxo Welcome, Bristol Meyers Squib, Monsanto/Searle, Eli Lilly, Novartis and Pharmacia UpJohn, or alternatively the potential ligand is synthesized de novo. As mentioned above, the de novo synthesis of one or even a relatively small group of specific compounds is reasonable in the art of drug design.

Alternatively, based on the molecular structures of the variable regions of the anti-Factor D antibodies, one could use molecular modeling and rational molecular design to generate and screen small molecules which mimic the molecular structures of the binding region of the antibodies and inhibit the activities of Factor D. These small molecules can be peptides, peptidomimetics, oligonucleotides, or organic compounds.

EXAMPLE

Efficacy of Antibody in a Laser-induced Choroidal Neovascularization (CNV) as a Model of Wet AMD The efficacy of intraocular injections of an antibody may be tested in a laser-injury CNV model as described earlier by Krzystolik M G et al. (Arch Ophthalm. 2002; 120: 338-346). This model may be used to test the efficacy of any drug candidate for the prevention and/or amelioration of AMD. This laser induced CNV model uses argon green laser to induce CNV in the monkey macula. There is a good correlation between the number of CNV lesions with significant angiographic leakage.

There are two phases of the studies: Phase 1, the prevention phase, involves the initiation of antibody treatment before laser induction of the CNV and 1 week after exposure to the laser to inhibit the formation of CNV, which typically appears 2 to 3 weeks after laser injury. Phase 2, the treatment phase, is initiated on day 42 (3 weeks after laser injury) when CNV lesions would be expected in the control eyes from phase 1. Phase 2 assesses the effect of treatment on attenuating the extent and leakiness of existing CNV lesions.

Ten cynomolgus monkeys (Macaca fascicularis) are typically used in a study of this type. The monkeys are anesthetized for all procedures with intramuscular injections of, e.g., ketamine hydrochloride (20 mg/kg); acepromazine maleate (0.125 mg/kg); and atropine sulfate (0.125 mg/kg). Supplemental anesthesia of 5 to 6 mg/kg of ketamine hydrochloride may be administered as needed. In addition, 0.5% proparacaine hydrochloride is typically used for topical anesthesia. Supplemental anesthesia, with intravenous pentobarbital sodium solution (5 mg/kg), may be administered before enucleation. Animals are euthanized following the experimentation.

Antibody Treatment

The antibody to be tested is administered in a physiological buffer at a concentration of about e.g., 10 µg/µL. The control eye is injected with a vehicle consisting of all components except the antibody to be tested. Intraocular injections of about, e.g., 50 µL per eye with either antibody or vehicle is performed on each eye, respectively, through the pars plana using a 30-gauge needle and tuberculin syringe after instilling topical anesthesia and 5% povidone iodine solution. The antibody is withdrawn from a vial through a 5-µm filter, and a new (sharp) 30-gauge needle is used for the intraocular injection. After the injection, a bacteriocidal ophthalmic ointment such as bacitracin is instilled in the fornices. The injection sites are typically varied to avoid trauma to the sclera.

In phase 1, the right or left eye of each animal is randomly assigned to receive intraocular injections of antibody at a dose of about, e.g., 500 µg (50 µL per eye), and this eye is termed the prevention eye. The dose used may be determined based on a safety and toxicology study prior to this efficacy study, or by other clinically appropriate means. The other eye is assigned to receive intraocular injections of vehicle and is termed the control eye. Both eyes of each animal typically receive two intraocular injections with either the antibody to be tested or the vehicle alone on days 0 and 14 before laser treatment. On day 21, all eyes undergo an argon green laser photocoagulation to induce CNV lesions. On day 28, one week after laser induction, the prevention eye receives another injection of antibody and the control eye receives vehicle. Phase 2 of the study begins on day 42 or 3 weeks after laser induction, when CNV is expected to have developed. Following fluorescein angiography on day 42, both eyes of each animal will receive intraocular injections of antibody at a dose of about, e.g., 500 µg (50 µL per eye), and this is repeated on day 56.

Induction of Experimental CNV

The CNV membranes are induced in the macula of cynomolgus monkeys with argon green laser burns (Coherent Argon Dye Laser 920; Coherent Medical Laser, Palo Alto, Calif.) using a slit-lamp and a plano fundus contact lens. Nine lesions are symmetrically placed in the macula of each eye by a masked surgeon. The laser variables include a 50- to 100-µm spot size, 0.1-second duration, and power ranging from 350 to 700 mW. The power used is determined by the laser's ability to produce a blister and a small hemorrhage under the power chosen. If no hemorrhage is noted, an additional laser spot will be placed adjacent to the first spot following the same laser procedure. Color photographs and fluorescein angiography are typically used to detect and measure the extent and leakiness of the CNV. However, any method capable of measuring laser-induced CNV and its associated effects may be used.

Ocular Examinations

The eyes of the animals are checked for relative pupillary afferent defect and then dilated with 2.5% phenylephrine hydrochloride and 0.8% tropicamide. Both eyes are examined using slitlamp biomicroscopy and indirect ophthalmoscopy on days 0, 14, 28, 42, and 56 (before antibody injection); days 1, 15, 29, 43, and 57 (after injection); day 21 (before laser); days 35 and 49 (intermediate days); and day 63 (enucleation and death).

Color Photography and Fluorescein Angiography

Fundus photography is typically performed on all animals on the same days as the ocular examination. Photographs may be obtained with a fundus camera (Canon Fundus CF-60Z; Canon USA Inc, Lake Success, N.Y.) and 35-mm film, but any photography device may be used.

The Imagenet Digital Angiography System (Topcon 501 A and Imagenet system; Topcon America Corp, Paramus, N.J.) may be used for fluorescein angiography. Red-free photographs of both eyes is typically obtained followed by fluorescein angiography using 0.1 mL/kg of body weight of 10% sodium fluorescein (Akorn Inc, Abita Springs, La.) at a rate of 1 mL/s. Following the fluorescein injection, a rapid series of images is obtained in the first minute of the posterior pole of first the right eye and then the left eye. Additional pairs of images are typically obtained at approximately 1 to 2 and 5 minutes. Between 2 and 5 minutes, two images of the mid-peripheral fields (temporal and nasal) are taken of each eye. Fluorescein angiography is performed at baseline (day 0) and days 7, 14, 29, 42, 49, 57, and 63.

Analysis of Ophthalmic Data

Photographs and angiograms are evaluated for evidence of angiographic leakage, hemorrhages, or any other abnormalities. The fundus hemorrhages are graded based on a grading system with retinal hemorrhages that involves less than 3 disc areas defined as grade 1, hemorrhages between 3 and 6 disc areas defined as grade 2, and hemorrhages of more than 6 disc areas defined as grade 3. The association of hemorrhages with CNV membranes or the laser induction site is also assessed. Clinically significant bleeding is defined as any fundus hemorrhage greater than or equal to a 6-disc area.

Ocular inflammation is also assessed using a slit-lamp biomicroscopy. Anterior chamber and vitreal cells are counted with a 2-mm slit-lamp at a high magnification and graded using the schema of the American Academy of Ophthalmology. The CNV lesions are graded by reviewing fluorescein angiograms performed on days 35, 42, 49, 56, and 63 by experienced examiners, typically two, who grade by consensus opinion. The CNV lesions are graded according to the following scheme, using standardized angiographs for comparison. Grade 1 lesions have no hyperfluorescence. Grade 2 lesions exhibit hyperfluorescence without leakage. Grade 3 lesions show hyperfluorescence in the early or mid-transit images and late leakage. Grade 4 lesions show bright hyperfluorescence in the transit and late leakage beyond the treated areas. Grade 4 lesions are defined as clinically significant.

Statistical analysis may be performed using the Population-Aggregated Panel Data with Generalized Estimating Equations and the incidence rate ratio (IRR). The incidence rate is usually defined as the number of grade 4 lesions that occur during a given interval divided by the total number of lesions induced. In phase 1, the IRR refers to the ratio of incidence rate of grade 4 lesions in the prevention eyes to the incidence rate in control eyes. An IRR of 1 signifies no difference between incidence rates. A number much smaller than 1 will indicate a reduction in the incidence of grade 4 lesions in the prevention group vs. control group. In phase 2, the incidence of grade 4 lesions in the control eyes vs. the treatment eyes is compared. This means that the incidence of grade 4 lesions is compared over time in the set of eyes that are first assigned to the control group but on days 42 and 56 are treated with antibody and become treatment eyes.

Screen for Agents Useful in the Treatment of AMD

The study and treatment of age-related macular degeneration (AMD) can be accomplished using a new animal model comprising mice deficient either in monocyte chemoattractant protein-1 (Ccl-2; also known as MCP-1) or its cognate C—C chemokine receptor-2 (Ccr-2) (Ambati, J. et al. Nat Med. 2003 November; 9(11):1390-7. Epub 2003 Oct 19). These mice develop cardinal features of AMD, including accumulation of lipofuscin in and drusen beneath the retinal pigmented epithelium (RPE), photoreceptor atrophy and choroidal neovascularization (CNV).

Treatment of these mice with a desired agent may allow assessment of the efficacy of such an agent for its efficacy in treating AMD.

We claim:

1. A method for ameliorating macular degeneration, comprising administering an effective amount of a complement inhibitor to a subject in need thereof, wherein the complement inhibitor is an antibody or antigen-binding fragment thereof, wherein the antibody or antigen-binding fragment specifically binds to Factor D.

2. The method of claim 1, wherein the subject requires inhibition of ocular neovascularization that affects the choroid, retinal pigmented epithelium, or retinal tissue.

3. The method according to claim 1, wherein the antigen-binding fragment comprises a Fab, Fab', F(ab')$_2$, Fv, a single chain Fv, a diabody, or a single domain antibody.

4. The method according to claim 1, wherein the antibody is a monoclonal antibody.

5. The method according to claim 1, wherein the antibody is a chimeric antibody, a multispecific antibody, a deimmunized antibody, a humanized antibody, a primatized antibody or a human antibody.

6. The method according to claim 1, wherein the antibody or antigen-binding fragment thereof comprises a therapeutic moiety.

7. The method of claim 6, wherein the therapeutic moiety is a cytotoxin, a therapeutic agent or a radioactive metal ion.

8. The method according to claim 1, wherein the antibody is monoclonal antibody 166-32 produced from the hybridoma deposited with the ATCC and designated HB 12476.

9. The method according to claim 1, wherein the antibody specifically binds to the same epitope as monoclonal antibody 166-32 produced from the hybridoma deposited with the ATCC and designated HB 12476.

10. The method according to claim 1, wherein the antibody is a humanized monoclonal antibody derived from monoclonal antibody 166-32 produced from the hybridoma deposited with the ATCC and designated HB 12476.

11. The method of claim 1, wherein the complement inhibitor is administered by parenteral administration, intradermal administration, intramuscular administration, intraperitoneal administration, intravenous administration, subantaneous administration, intranasal administration, oral administration, enteral administration, topical administration, intrathecal administration, intraventricular administration, epidural , inhalation, a biocompatible or bioerodable sustained release implant, or implantation of an infusion pump.

12. The method of claim 1, wherein the complement inhibitor is administered locally.

13. The method of claim 1, wherein the complement inhibitor is administered by intraocular administration, intravitreal administration, or subconjunctival administration.

14. The method according to claim 1, wherein the complement inhibitor is administered in an eye wash solution, an eye ointment, an eye shield or an eye drop solution.

15. The method according to claim 1, further comprising the step of administering an immunomodulatory compound, an immunosuppressive compound, an anti-inflammatory compound, or an anti-angiogenic compound, to said subject.

16. The method of claim 1, further comprising administering to the subject an anti-angiogenesis therapy targeting vascular endothelial growth factor (VEGF).

17. The method of claim 1, wherein the dosage of complement inhibitor administered to the subject is between 0.1 mg/kg to 100 mg/kg.

18. The method of claim 1, wherein the macular degeneration is dry form of age-related macular degeneration.

19. The method of claim 1, wherein the subject is human.

20. A method for inhibiting the alternative pathway activation in a subject with macular degeneration, comprising administering to the subject an effective amount of an antibody or antigen-binding fragment thereof, wherein the antibody or antigen-binding fragment specifially binds to Factor D.

21. The method of claim 20, wherein the subject requires inhibition of ocular neovascularization that affects the choroid, retinal pigmented epithelium, or retinal tissue.

22. The method of claim 20, wherein the antigen-binding fragment comprises a Fab, Fab', F(ab')$_2$, Fv, a single chain Fv, a diabody, or a single domain antibody.

23. The method of claim 20, wherein the antibody is a monoclonal antibody.

24. The method of claim 20, wherein the antibody is a chimeric antibody, a multispecific antibody, a deimmunized antibody, a humanized antibody, a primatized antibody or a human antibody.

25. The method of claim 20, wherein the antibody or antigen-binding fragment thereof comprises a therapeutic moiety.

26. The method of claim 20, wherein the antibody is monoclonal antibody 166-32 produced from the hybridoma deposited with the ATCC and designated HB 12476.

27. The method of claim 20, wherein the antibody specifically binds to the same epitope as monoclonal antibody 166-32 produced from the hybridoma deposited with the ATCC and designated HB 12476.

28. The method according to claim 20, wherein the antibody is a humanized monoclonal antibody derived from monoclonal antibody 166-32 produced from the hybridoma deposited with the ATCC and designated HB 12476.

29. The method of claim 20, wherein the antibody or the antigen-binding fragment thereof is administered by parenteral administration, intradermal administration, intramuscular administration, intraperitoneal administration, intravenous administration, subantaneous administration, intranasal administration, oral administration, enteral administration, topical administration, intrathecal administration, intraventricular administration, epidural , inhalation, a biocompatible or bioerodable sustained release implant, or implantation of an infusion pump.

30. The method of claim 20, wherein the antibody or the antigen-binding fragment thereof is administered locally.

31. The method of claim 20, wherein the antibody or the antigen-binding fragment thereof is administered by intraocular administration, intravitreal administration, or subconjunctival administration.

32. The method according to claim 20, wherein the antibody or the antigen-binding fragment thereof is administered in an eye wash solution, an eye ointment, an eye shield or an eye drop solution.

33. The method according to claim 20, further comprising the step of administering an immunomodulatory compound, an immunosuppressive compound, an anti-inflammatory compound, or an anti-angiogenic compound, to said subject.

34. The method of claim 20, further comprising administering to the subject an anti-angiogenesis therapy targeting vascular endothelial growth factor (VEGF).

35. The method of claim 20, wherein the dosage of the antibody or the antigen-binding fragment thereof administered to the subject is between 0.1 mg/kg to 100 mg/kg.

36. The method of claim 25, wherein the therapeutic moiety is a cytotoxin, a therapeutic agent or a radioactive metal ion.

37. The method of claim 20, wherein the macular degeneration is dry form of age-related macular degeneration.

38. The method of claim 20, wherein the subject is human.

* * * * *

UNITED STATES PATENT AND TRADEMARK OFFICE
CERTIFICATE OF CORRECTION

| | | |
|---|---|---|
| PATENT NO. | : 8,753,625 B2 | Page 1 of 1 |
| APPLICATION NO. | : 12/092346 | |
| DATED | : June 17, 2014 | |
| INVENTOR(S) | : Fung et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1188 days.

Signed and Sealed this
Eighth Day of September, 2015

Michelle K. Lee
*Director of the United States Patent and Trademark Office*